ns(12) United States Patent
Yamaji et al.

(10) Patent No.: US 7,193,073 B2
(45) Date of Patent: Mar. 20, 2007

(54) AGGRECANASE

(75) Inventors: Noboru Yamaji, Ibaraki (JP); Kouichi Nishimura, Ibaraki (JP); Kunitake Abe, Ibaraki (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 11/285,804

(22) Filed: Nov. 23, 2005

(65) Prior Publication Data

US 2006/0078957 A1    Apr. 13, 2006

Related U.S. Application Data

(62) Division of application No. 10/240,545, filed as application No. PCT/JP01/11033 on Dec. 17, 2001, now Pat. No. 7,094,590.

(30) Foreign Application Priority Data

Dec. 18, 2000 (JP) ............................. 2000-384300

(51) Int. Cl.
*C12N 15/63* (2006.01)
*C12N 1/21* (2006.01)
*C12N 5/06* (2006.01)
*C12N 9/64* (2006.01)

(52) U.S. Cl. .................. 536/23.2; 435/226; 435/252.3; 435/320.1; 435/325

(58) Field of Classification Search ............... None
See application file for complete search history.

(56) References Cited

U.S. PATENT DOCUMENTS

| 6,326,162 B1 | 12/2001 | Miller et al. | |
| 2003/0185828 A1 | 10/2003 | Yamaji et al. | |
| 2004/0018555 A1* | 1/2004 | Anderson et al. | 435/7.1 |
| 2004/0053269 A1* | 3/2004 | Todd et al. | 435/6 |

FOREIGN PATENT DOCUMENTS

| AU | 9885131 A | 2/1999 |
| EP | 998572 A2 | 2/1999 |
| JP | 2001-511351 A | 8/2001 |
| JP | 2003-144154 A | 5/2003 |
| WO | WO 99/05291 A2 | 2/1999 |
| WO | WO 03/027282 A1 | 4/2003 |

OTHER PUBLICATIONS

Apte (Dec. 1, 2000) GenBank accession AF163762.*
Abbaszade et al., "Cloning and Characterization of ADAMTS11, an Aggrecanase from the ADAMTS Family," J. Biological Chemistry, 1999, 274(33): 23443-23450.
Chapman et al., "Osteoarthritis-Susceptibility Locus on Chromosome 11q, Detected by Linkage," Am. J. Hum. Genet., 1999, 65: 167-174.
Flannery et al., "Expression of ADAMTS Homologues in Articular Cartilage," Biochem. Biophys. Res. Comm., 1999, 260: 318-322.
Loughlin et al., "Stratification Analysis of an Osteoarthritis Genome Screen-Suggestive Linkage to Chromosomes 4, 6, and 16," Am. J. Hum. Genet., 1999, 65:1795-1798.
Tortorella et al., "Purification and Cloning of Aggrecanase-1: A Member of the ADAMTS Family of Proteins," Science, 1999, 284: 1664-1666.
International Search Report for PCT Application PCT/JP01/11033, mailed Mar. 19, 2002.
Supplementary European Search Report for Application No. EP 01 27 1116, mailed Apr. 4, 2004.
Apte (Dec. 1, 2000) GenBank Accession AF163762.
Preliminary Amendment mailed Feb. 14, 2003, for U.S. Appl. No. 10/240,545.
Office Action mailed May 5, 2005, for U.S. Appl. No. 10/240,545.
Reply to Office Action mailed Aug. 4, 2005, for U.S. Appl. No. 10/240,545.
Notice of Allowance and Fee(s) Due mailed Sep. 21, 2005, for U.S. Appl. No. 10/240,545.

* cited by examiner

*Primary Examiner*—Elizabeth Slobodyansky
(74) *Attorney, Agent, or Firm*—Finnegan, Henderson, Farabow, Garrett, & Dunner, L.L.P.

(57) ABSTRACT

A novel polypeptide, a polynucleotide encoding this polypeptide, an expression vector comprising this polynucleotide, a cell transfected with the expression vector, an antibody binding to the above polypeptide, a convenient screening method for obtaining an agent for treating joint diseases, and a process for manufacturing a pharmaceutical composition for treating joint diseases are disclosed.

The polypeptide is a novel aggrecanase causative of joint diseases (particularly an OA disease).

3 Claims, No Drawings

AGGRECANASE

This is a division of application Ser. No. 10/240,545, filed Oct. 2, 2002 now U.S. Pat. No. 7,094,590, which is a National Stage of International Application PCT/JP01/11033, filed Dec. 17, 2001 under 35 U.S.C. 371, both of which are incorporated herein by reference.

TECHNICAL FIELD

The present invention relates to a novel aggrecanase.

BACKGROUND ART

Joint diseases are diseases which show damage and degeneration of joint cartilage as the main morbid states. Though a disease having the most frequent number of patients among joint diseases is osteoarthritis (OA) (Elders M. J., J. Rheumatol., 27, Suppl., 60, 6–8, 2000), analgesic anti-inflammatory drugs and hyaluronic acid preparations are used in the current therapeutic method merely as a symptomatic therapy for the purpose of alleviating pains accompanied by the degeneration of cartilage and the destruction of subchondral cartilage, so that it cannot be said that they are exerting sufficient therapeutic effects (Dieppe P., Scand. J. Rheumatol., 29, 279–281, 2000).

Joint cartilage is a tissue mainly composed of type II collagen and aggrecan which is a cartilage-specific proteoglycan, and degradation and degeneration of both of them are observed in the joint diseases. Because of this, it has been considered for a long time that control of the degradation and degeneration of these extracellular matrix components would lead to the treatment of joint diseases, so that attempts have been positively made to identify degradation-concerned proteases (collagenase and aggrecanase) and to screen their inhibitors and develop them as medicaments.

As proteases having collagenase activities, matrix metalloproteases (MMP1, MMP8, MMP13, MMP14 and the like) have been identified, and their selective inhibitors have been discovered. However, in spite of the attempts to develop a large number of MMP inhibitors having collagenase inhibition activities as therapeutic drugs for joint diseases including OA and rheumatic arthritis (RA), MMP inhibitors to be used in these diseases as the indication have not been put on the market (Greenwald R. A., Ann. New York Acad. Sci., 878, 413–419, 1999). Under such circumstances, attention has been directed toward aggrecanase which selectively degrades aggrecan which is another main constituting component of joint cartilage.

A joint disease-related role of an enzyme aggrecanase which cleaves aggrecan at the site between Glu373-Ala374 has been revealed by the reports of Sandy et al. and Lohmander et al. stating that all of the main digested aggrecan fragments found in the synovial fluid of human arthritis patients were generated by cleaving at the aggrecanase digestion site (Sandy J. D. et al., J. Clin. Invest., 89, 1512–1516, 1992; Lohmander L. S. et al., Arthritis Rheum., 36, 1214–1222, 1993). On the other hand, it has been known that, in an in vitro explant culture system of joint cartilage, degradation of aggrecan firstly occurs by IL-1 induction and then degradation of type II collagen is accelerated (Dingle L. T. et al., Ann. Rheum. Dis., 34, 303–311, 1975; Cawston T. E. et al., Biochem. Biophys. Res. Comm., 215, 377–385, 1995; Kozaci L. D. et al., Arthritis Rheum., 40, 164–174, 1997). It has been reported that the aggrecan degradation takes the precedence of the type II collagen degradation in a mouse arthritis model too (van Meurs J. B. et al., Arthritis Rheum., 42, 1128–1139, 1999). These reports suggest a possibility that the type II collagen degradation can be controlled by inhibiting the preceding aggrecan degradation.

However, although biochemical features show that it is a metalloprotease, that it is located on the outside of cells, that sugar chains contribute to a substrate recognition, and that an activity is induced by IL-1, TNF, or retinoic acid, aggrecanase as a cause of joint diseases has been unidentified for a long time. Recently, ADAMTS4 (aggrecanase-1; Tortorella M. D. et al., Science, 284, 1664–1666, 1999) and ADAMTS11 (aggrecanase-2; Abbaszade I. et al., J. Biol. Chem., 274, 23443–23450, 1999) were reported as the protease having the aggrecanase activity. However, the gene expressions of these proteases are not increased in human OA cartilage and not induced by IL-1, TNF, or retinoic acid (it is known that these compounds induce the aggrecanase activity in an explant culture system of human knee articular cartilage), and thus the presence of another protease relating to joint diseases was suggested (Flannery C. R. et al., Biochem. Biophys. Res. Commun., 260, 318–322, 1999).

In addition, recently, chromosomal loci in which genetic factors relating to OA are located (an OA-susceptibility locus) in accordance with a genetic research for patients suffering from OA or families having a strong family history of OA have been identified. For example, 11q (Chapman K. et al., Am. J. Hum. Genet., 65, 167–174, 1999), 4q12–4q21.2, 6q21.1–6q22.1, 16p13.1–16q12.1, and 16q21–16q23 (Loughlin J. et al., Am. J. Hum. Genet., 65, 1795–1798, 1999) are reported as the OA-susceptibility loci.

DISCLOSURE OF INVENTION

The object of the present invention is to provide a novel aggrecanase causative of joint diseases, which is useful as a screening tool for an agent for treating joint diseases, a novel polynucleotide encoding the aggrecanase, and a convenient screening system for obtaining a substance useful as an agent for treating joint diseases.

With the aim of solving the aforementioned problems, the present inventors have conducted intensive studies and, as a result, obtained a gene encoding an aggrecanase [i.e., MDTS8 (Metalloprotease and Disintegrin with Thrombospondin type-1 repeats 8)] causative of joint diseases, and expressed the aggrecanase protein. The inventors showed that the protein exhibits an aggrecanase activity, that the expression of the protein is induced by differentiation to cartilage cells, and that the chromosomal location of MDTS8 is in the locus which is identified as an OA (one of joint diseases) susceptibility locus, and thus confirmed that the polypeptide of the present invention is an aggrecanase causative of joint diseases and useful as a screening tool for an agent for treating joint diseases. Further, the inventors established a method for detecting whether or not a compound to be tested inhibits an aggrecanase activity causative of joint diseases using the protein, and a method for screening an agent for treating joint diseases using the detecting method. Furthermore, the inventors established a process for manufacturing a pharmaceutical composition for treating joint disease comprising the detection step, and completed the present invention.

Accordingly, the present invention relates to:

[1] a polypeptide exhibiting an aggrecanase activity and comprising (1) an amino acid sequence of SEQ ID NO: 2 or (2) an amino acid sequence in which 1 to 10 amino acids are deleted, substituted, and/or inserted in an amino acid sequence of SEQ ID NO: 2;

[2] the polypeptide of the item [1], comprising an amino acid sequence of SEQ ID NO: 2, and exhibiting an aggrecanase activity;
[3] a polypeptide comprising an amino acid sequence in which one or plural amino acids are deleted, substituted, and/or inserted in an amino acid sequence of SEQ ID. NO: 2 and of which an expression is induced by differentiation to cartilage cells, and exhibiting an aggrecanase activity;
[4] a polypeptide comprising an amino acid sequence having a 90% or more homology with an amino acid sequence of SEQ ID NO: 2, and exhibiting an aggrecanase activity;
[5] a polypeptide consisting of an amino acid sequence of SEQ ID NO: 2;
[6] a polynucleotide encoding the polypeptide of the items [1] to [5];
[7] an expression vector comprising the polynucleotide of the item [6];
[8] a cell transfected with the expression vector of the item [7];
[9] a method for detecting whether or not a compound to be tested inhibits an aggrecanase activity of a polypeptide of the items [1] to [5], comprising the steps of:
bringing into contact (1) said polypeptide, (2) a substrate polypeptide capable of digesting with aggrecanase, and (3) the compound to be tested; and
analyzing a digestion of the substrate polypeptide;
[10] a method for screening a substance which inhibits an aggrecanase activity of a polypeptide of the items [1] to [5], comprising the steps of:
detecting by the method of the item [9]; and
selecting a substance inhibiting an aggrecanase activity
[11] a method for screening a substance for treating joint diseases by the method of the item [10];
[12] a process for manufacturing a pharmaceutical composition for treating joint diseases, comprising the steps of:
detecting by the method of the item [9]; and
preparing a medicament; and
[13] an antibody or a fragment thereof, which binds to the polypeptide of the items [1] to [5].

The term "aggrecan" as used herein means a proteoglycan which is located in an extracellular matrix of articular cartilage and consists of a core protein comprising two spherical domains (G1 and G2) at the N-terminus, glycosaminoglycan-binding region, and a spherical domain (G3) at the C-terminus, and chondroitin sulfate and glycosaminoglycan keratan sulfate which modify the core protein.

The term "aggrecanase activity" as used herein means an activity of selectively digesting human aggrecan present in articular cartilage between the 373rd glutamic acid residue and the 374th alanine residue (hereinafter referred to as "between $Glu^{373}$-$Ala^{374}$").

The term "aggrecanase" as used herein means a metalloprotease exhibiting the aggrecanase activity. The aggrecanase generally has a zinc-binding consensus sequence [i.e., His-Glu-Xaa-Xaa-His (Xaa means an arbitrary amino acid.); the sequence of SEQ ID NO: 24].

BEST MODE FOR CARRYING OUT THE INVENTION

The present invention will be explained in detail hereinafter.

[1] The Polypeptide of the Present Invention
The polypeptide of the present invention includes
(1) a polypeptide consisting of the amino acid sequence of SEQ ID NO: 2;
(2) a polypeptide comprising the amino acid sequence of SEQ ID NO: 2, and exhibiting the aggrecanase activity;
(3) a polypeptide comprising an amino acid sequence in which one or plural amino acids are deleted, substituted, and/or inserted at one or plural positions in the amino acid sequence of SEQ ID NO: 2, and exhibiting the aggrecanase activity (hereinafter referred to as a variation functionally equivalent); and
(4) a polypeptide comprising an amino acid sequence having a 90% or more homology with the amino acid sequence of SEQ ID NO: 2, and exhibiting the aggrecanase activity (hereinafter referred to as a homologous polypeptide).

Among the polypeptides (1) to (4) as the polypeptide of the present invention, a polypeptide comprising an amino acid sequence of which an expression is induced by differentiation to cartilage cells is preferable.

(1) The Polypeptide Consisting of the Amino Acid Sequence of SEQ ID NO: 2

As the polypeptide of the present invention, the polypeptide consisting of the amino acid sequence of SEQ ID NO: 2 is most preferable. The polypeptide consisting of the amino acid sequence of SEQ ID NO: 2 exhibits the aggrecanase activity and is a novel human aggrecanase consisting of 1221 amino acid residues. As shown in Example 5, the expression of the polypeptide is induced by differentiation to cartilage cells. Further, as shown in Example 6, the gene thereof is located in a chromosome relating to osteoarthritis (OA), and thus it is considered that the polypeptide consisting of the amino acid sequence of SEQ ID NO: 2 is an aggrecanase causative of joint diseases.

(2) The Polypeptide Comprising the Amino Acid Sequence of SEQ ID NO: 2, and Exhibiting the Aggrecanase Activity The "polypeptide comprising the amino acid sequence of SEQ ID NO: 2 and exhibiting the aggrecanase activity" as the polypeptide of the present invention includes, for example, the polypeptide consisting of the amino acid sequence of SEQ ID NO: 2, and a polypeptide in which an appropriate marker sequence or the like is added to the N-terminus and/or the C-terminus of the polypeptide having the amino acid sequence of SEQ ID NO: 2 (i.e., a fusion polypeptide having an amino acid sequence in which an appropriate marker sequence or the like is added to the N-terminus and/or the C-terminus of the amino acid sequence of SEQ ID NO: 2).

As the marker sequence, a sequence for easily carrying out confirmation of polypeptide expression., confirmation of intracellular localization thereof, purification thereof, or the like may be used. As the sequence, there may be mentioned, for example, a FLAG tag, a hexa-histidine tag (i.e., a His tag), a hemagglutinin tag, or a myc epitope.

A method for confirming whether or not a polypeptide to be tested exhibits the "aggrecanase activity" as used herein (hereinafter sometimes referred to as a "method for confirming the aggrecanase activity") is not particularly limited. It may be confirmed, for example, by bringing a polypeptide to be tested (such as cells, a tissue culture supernatant, or a tissue extract containing the test polypeptide, or a purified or partial purified preparation of the test polypeptide) into contact with a substrate of aggrecanase (such as human aggrecan) in an appropriate buffer [such as 50 mmol/L Tris-HCl (pH7.4)], and then analyzing whether or not the substrate is digested at the cleavage site (for example, between $Glu^{373}$-$Ala^{374}$ in human aggrecan), preferably by a method described in Example 4.

The substrate of aggrecanase is not particularly limited, so long as it is a polypeptide capable of being digested with aggrecanase (hereinafter referred to as a substrate polypeptide), but there may be mentioned, for example, aggrecan derived from human or other animals, a fragment of the aggrecan (a fragment capable of being digested with aggrecanase), or a fusion polypeptide of the aggrecan or the fragment thereof and an appropriate marker sequence (such as a FLAG tag, a His tag, a hemagglutinin tag, or a myc epitope, preferably a FLAG tag or a His tag) (a fusion polypeptide capable of being digested with aggrecanase). More particularly, for example, purified aggrecans from human or other animals cartilage tissue, recombinant aggrecans (such as recombinant aggrecan obtained by adding a FLAG tag to the N-terminus and a His tag to the C-terminus of aggrecan or a fragment thereof, respectively), commercially available aggrecans (SEIKAGAKU CORPORATION), or partial polypeptides of these aggrecans may be used.

As a method for analyzing whether or not the substrate polypeptide is digested by the aggrecanase activity, there may be mentioned, for example, a method for analyzing a polypeptide fragment generated by digesting the substrate polypeptide with the test polypeptide (such as a method for detecting the presence of the polypeptide fragment, or a method for measuring an amount of the generated polypeptide fragment), or a method for analyzing the substrate polypeptide decreased by the digestion (such as a method for detecting the presence of the substrate polypeptide, or a method for measuring an amount of the decreased substrate polypeptide).

For example, in the case of using human aggrecan as the substrate polypeptide, a method for analyzing a polypeptide fragment generated by digesting aggrecan between $Glu^{373}$-$Ala^{374}$ is not particularly limited, but, for example, a method for determining a N-terminus sequence or a C-terminus sequence of the digested fragment by a conventional method, or more conveniently, immunological methods such as ELISA (Enzyme Linked Immuno Solvent Assay) or a western blotting method using an anti-neoepitope antibody (Hughes C. E. et al., Biochem. J., 305, 799–804, 1995) which specifically recognizes an $Asn^{369}$-$Ile^{370}$-$Thr^{372}$-$Gly^{372}$-$Glu^{373}$ sequence (the sequence of SEQ ID NO: 25) at the C-terminus or an $Ala374$-$Arg^{375}$-$Gly^{376}$-$Ser^{377}$-$Val^{378}$ sequence (the sequence of SEQ ID NO: 26) at the N-terminus generated by digesting aggrecan between $Glu^{373}$-$Ala^{374}$ may be used. The immunological methods such as ELISA or a western blotting method may be carried out in accordance with, for example, Migita, S., Konda, S., Honjo, T, Hamaoka, T., "Men-eki Jikken Sousa Hou (Methods in Immulogical Experiments) I,II", Nanko-do, 1995.

Further, in the case of using human aggrecan as the substrate polypeptide, the method for analyzing human aggrecan decreased by digesting aggrecan between $Glu^{373}$-$Ala374$ is not particularly limited, but for example, a western blotting method using an anti-human aggrecan antibody may be used.

Furthermore, in the case of using the recombinant aggrecan obtained by adding a FLAG tag to the N-terminus and a His tag to the C-terminus of aggrecan or a fragment thereof, respectively, ELISA or a western blotting method using an anti-FLAG tag antibody and/or an anti-His tag antibody may be used as the method for analyzing the recombinant aggrecan decreased by digesting aggrecan between $Glu^{373}$-$Ala^{374}$.

(3) The Variation Functionally Equivalent

The variation functionally equivalent of the present invention is not particularly limited, so long as it is a polypeptide comprising an amino acid sequence in which one or plural (preferably 1 to 10, more preferably 1 to 7, most preferably 1 to 5) such as 1 or several amino acids are deleted, substituted, and/or inserted at one or plural positions in the amino acid sequence of SEQ ID NO: 2 and exhibiting the aggrecanase activity (preferably further comprising an amino acid sequence of which an expression is induced by differentiation to cartilage cells). Further, an origin of the variation functionally equivalent is not limited to a human.

The variation functionally equivalent of the present invention includes, for example, human variations of the polypeptide having the amino acid sequence of SEQ ID NO: 2 and variations functionally equivalent derived from organisms other than a human (such as a mouse, a rat, a hamster, or a dog), and further polypeptides obtained by artificially modifying these native polypeptides (i.e., human variations or variations functionally equivalent derived from organisms other than a human) or the polypeptide having the amino acid sequence of SEQ ID NO: 2 by genetic engineering techniques. The term "variation" as used herein means an individual difference between the same polypeptides in the same species or a difference between homologous polypeptides in several species.

Human variations of the polypeptide consisting of the amino acid sequence of SEQ ID NO: 2 or variations functionally equivalent derived from organisms other than a human may be obtained by those skilled in the art in accordance with the information of a base sequence (for example, the base sequence of SEQ ID NO: 1) of a polynucleotide encoding the polypeptide consisting of the amino acid sequence of SEQ ID NO: 2. In this connection, genetic engineering techniques may be generally performed in accordance with known methods (for example, Sambrook, J. et al., "Molecular Cloning—A Laboratory Manual", Cold Spring Harbor Laboratory, NY, 1989).

For example, an appropriate probe or appropriate primers are designed in accordance with the information of a base sequence of a polynucleotide encoding the polypeptide consisting of the amino acid sequence of SEQ ID NO: 2. A polymerase chain reaction (PCR) method (Saiki, R. K. et al., Science, 239, 487–491, 1988) or a hybridization method is carried out using a sample (for example, total RNA or an mRNA fraction, a cDNA library, or a phage library) prepared from an organism (for example., a mammal such as a human, a mouse, a rat, a hamster, or a dog) of interest and the primers or the probe to obtain a polynucleotide encoding the polypeptide. A desired polypeptide may be obtained by expressing the resulting polynucleotide in an appropriate expression system and confirming that the expressed polypeptide exhibits the aggrecanase activity by, for example, the method described in Example 4.

Further, the polypeptide artificially modified by genetic engineering techniques may be obtained by, for example, the following procedure. A gene encoding the polypeptide is obtained by a conventional method such as site-directed mutagenesis (Mark, D. F. et al., Proc. Natl. Acad. Sci. USA, 81, 5662–5666; 1984). A desired polypeptide may be obtained by expressing the resulting polynucleotide in an appropriate expression system and confirming that the expressed polypeptide exhibits the aggrecanase activity by, for example, the method described in Example 4.

The variation functionally equivalent of the present invention includes a fusion polypeptide exhibiting the aggrecanase activity and having an amino acid sequence in which one or plural amino acids are deleted, substituted, and/or inserted at one or plural positions in the amino acid sequence of SEQ ID NO: 2 and an appropriate marker sequence or the like is added to the N-terminus and/or the C-terminus thereof.

Further, as the variation functionally equivalent of the present invention, a polypeptide consisting of an amino acid sequence in which one or plural (preferably 1 to 10, more preferably 1 to 7, most preferably 1 to 5) such as 1 or several amino acids are deleted, substituted, and/or inserted at one or plural positions in the amino acid sequence of SEQ ID NO: 2, and exhibiting the aggrecanase activity is preferable, and a polypeptide further comprising an amino acid sequence of which an expression is induced by differentiation to cartilage cells is more preferable.

(4) The Homologous Polypeptide

The homologous polypeptide of the present invention is not particularly limited, so long as it is a polypeptide having an amino acid sequence having a 90% or more homology with the amino acid sequence of SEQ ID NO: 2, and exhibiting the aggrecanase activity. The homologous polypeptide of the present invention may have an amino acid sequence having preferably a 95% or more homology, more preferably a 98% or more homology, most preferably a 99% or more homology, with respect to the amino acid sequence of SEQ ID NO: 2. As the homologous polypeptide of the present invention, a polypeptide consisting of an amino acid sequence having a 90% or more homology (preferably a 95% or more homology, more preferably a 98% or more homology, most preferably a 99% or more homology) and exhibiting the aggrecanase activity is preferable.

Further, as the homologous polypeptide of the present invention, a polypeptide exhibiting the aggrecanase activity and comprising an amino acid sequence of which an expression is induced by differentiation to cartilage cells is more preferable.

The term "homology" as used herein means a value obtained by a BLAST [Basic local alignment search tool; Altschul, S. F. et al., J. Mol. Biol., 215, 403–410, (1990)] search. The homology in the amino acid sequence may be calculated by a BLAST search algorithm. More particularly, it may be calculated using a bl2seq program (Tatiana A. Tatusova and Thomas L. Madden, FEMS Microbiol. Lett., 174, 247–250, 1999) in a BLAST package (sgi32bit edition, version 2.0.12; obtained from NCBI) in accordance with a default parameter. As a pairwise alignment parameter, a program "blastp" is used. Further, "0" as a Gap insertion cost value, "0" as A Gap elongation cost value, "SEG" as a filter for a Query sequence, and "BLOSUM62" as a Matrix are used, respectively.

[2] The Polynucleotide of the Present Invention

The polynucleotide of the present invention is not particularly limited, so long as it encodes the polypeptide of the present invention. As the polynucleotide of the present invention, there may be mentioned, for example, a polynucleotide comprising the base sequence of SEQ ID NO: 1. Such polynucleotide consisting of the base sequence of SEQ ID NO: 1 is most preferable. In this connection, the term "polynucleotide" as used herein includes both DNA and RNA.

A method for producing the polynucleotide of the present invention is not particularly limited, but there may be mentioned, for example, (1) a method using PCR, (2) a method using conventional genetic engineering techniques (i.e., a method for selecting a transformant comprising a desired cDNA from strains transformed with a cDNA library), or (3) a chemical synthesis method. These methods will be explained in this order hereinafter.

In the method using PCR of the item (1), the polynucleotide of the present invention may be produced, for example, by the following procedure.

mRNA is extracted from human cells or tissue capable of producing the polypeptide of the present invention. A pair of primers, between which full-length mRNA corresponding to the polypeptide of the present invention or a partial region of the mRNA is located, is synthesized on the basis of the base sequence of a polynucleotide encoding the polynucleotide of the present invention. Full-length cDNA encoding the polypeptide of the present invention or a part of the cDNA may be obtained by performing a reverse transcriptase-polymerase chain reaction (RT-PCR) using the extracted mRNA as a template.

More particularly, total RNA containing mRNA encoding the polypeptide of the present invention is extracted by a known method from cells or tissue capable of producing the polypeptide of the present invention. As an extraction method, there may be mentioned, for example, a guanidine thiocyanate-hot phenol method, a guanidine thiocyanate-guanidine hydrochloride method, or a guanidine thiocyanate-cesium chloride method. The guanidine thiocyanate-cesium chloride method is preferably used. The cells or tissue capable of producing the polypeptide of the present invention may be identified, for example, by a northern blotting method using a polynucleotide or a part thereof encoding the polypeptide of the present invention or a western blotting method using an antibody specific for the polypeptide of the present invention.

Next, the extracted mRNA is purified. Purification of the mRNA may be made in accordance with a conventional method. For example, the mRNA may be purified by adsorption and elution using an oligo(dT)-cellulose column. The mRNA may be further fractionated by, for example, a sucrose density gradient centrifugation, if necessary. Alternatively, commercially available extracted and purified mRNA may be used without carrying out the extraction of the mRNA.

Next, the first-strand cDNA is synthesized by carrying out a reverse transcriptase reaction of the purified mRNA in the presence of a random primer, an oligo dT primer, and/or a custom primer. This synthesis may be carried out in accordance with a conventional method. The resulting first-strand cDNA is subjected to PCR using two primers between which a full-length or a partial region of the polynucleotide of interest is located, thereby amplifying the cDNA of interest. The resulting DNA is fractionated by, for example, an agarose gel electrophoresis. The DNA fragment of interest may be obtained by carrying out a digestion of the DNA with restriction enzymes and subsequent ligation, if necessary.

In the method using conventional genetic engineering techniques of the item (2), the polynucleotide of the present invention may be produced, for example, by the following procedure.

First, single-stranded cDNA is synthesized by using reverse transcriptase from mRNA prepared by the above-mentioned PCR method as a template, and then double-stranded cDNA is synthesized from the single-stranded cDNA. As this method, there may be mentioned, for example, an S1 nuclease method (Efstratiadis, A. et al., Cell, 7, 279–288, 1976), a Land method (Land, H. et al., Nucleic Acids Res., 9, 2251–2266, 1981), an O. Joon Yoo method (Yoo, O. J. et al., Proc. Natl. Acad. Sci. USA, 79, 1049–1053, 1983), and an Okayama-Berg method (Okayama, H. and Berg, P., Mol. Cell. Biol., 2, 161–170, 1982).

Next, a recombinant plasmid comprising the double-stranded cDNA is prepared and introduced into an *Escherichia coli* strain, such as DH 5α, HB101, or JM109, thereby transforming the strain. A transformant is selected using a drug resistance against, for example, tetracycline, ampicillin, or kanamycin as a marker. When the host cell is *E. coli*, transformation of the host cell may be carried out, for example, by the method of Hanahan (Hanahan, D. J., Mol. Biol., 166, 557–580, 1983); namely, a method in which the recombinant DNA is added to competent cells prepared in the presence of $CaCl_2$, $MgCl_2$, or RbCl. Further, as a vector other than a plasmid, a phage vector such as a lambda system may be used.

As a method for selecting a transformant containing the cDNA of interest from the resulting transformants, various methods such as (i) a method for screening a transformant using a synthetic oligonucleotide probe, (ii) a method for screening a transformant using a probe produced by PCR, (iii) a method for screening a transformant using an antibody against the polypeptide of the present invention, or (iv) a method for screening a transformant using a selective hybridization translation system, may be used.

In the method of the item (i) for screening a transformant using a synthetic oligonucleotide probe, the transformant containing the cDNA of interest may be selected, for example, by the following procedure.

An oligonucleotide which corresponds to the whole or a part of the polypeptide of the present invention is synthesized (in this case, it may be either a nucleotide sequence taking the codon usage into consideration or a plurality of nucleotide sequences as a combination of possible nucleotide sequences, and in the latter case, their numbers can be reduced by including inosine) and, using this oligonucleotide as a probe (labeled with $^{32}P$ or $^{33}P$), hybridized with a nitrocellulose filter or a polyamide filter on which DNAs of the transformants are denatured and fixed, to screen and select resulting positive strains.

In the method of the item (ii) for screening a transformant using a probe produced by PCR, the transformant containing the cDNA of interest may be selected, for example, by the following procedure.

Oligonucleotides of a sense primer and an antisense primer corresponding to a part of the polypeptide of the present invention are synthesized, and a DNA fragment encoding the whole or a part of the polypeptide of interest is amplified by carrying out PCR using these primers in combination. As a template DNA used in this method, cDNA synthesized by a reverse transcription reaction from mRNA of cells capable of producing the polypeptide of the present invention, or genomic DNA, may be used. The resulting DNA fragment is labeled with $^{32}P$ or $^{33}P$, and a transformant containing the cDNA of interest is selected by carrying out a colony hybridization or a plaque hybridization using this fragment as a probe.

In the method of the item (iii) for screening a transformant using an antibody against the polypeptide of the present invention, the transformant containing the cDNA of interest may be selected, for example, by the following procedure.

First, cDNA is integrated into an expression vector, and polypeptides are produced into a culture supernatant, inside the cells, or on the cell surface of transformants. A transformant containing the cDNA of interest is selected by detecting a strain producing the desired polypeptide using an antibody against the polypeptide of the present invention and a second antibody against the first antibody.

In the method of the item (iv) for screening a transformant using a selective hybridization translation system, the transformant containing the cDNA of interest may be selected, for example, by the following procedure.

First, cDNA obtained from each transformant is blotted on, for example, a nitrocellulose filter and hybridized with mRNA prepared from cells capable of producing the polypeptide of the present invention, and then the mRNA bound to the cDNA is dissociated and recovered. The recovered mRNA is translated into a polypeptide in an appropriate polypeptide translation system, for example, injection into *Xenopus* oocytes or a cell-free system such as a rabbit reticulocyte lysate or a wheat germ. A transformant containing the cDNA of interest is selected by detecting it with the use of an antibody against the polypeptide of the present invention.

A method for collecting the polynucleotide of the present invention from the resulting transformant of interest can be carried out in accordance with a known method (for example, Sambrook, J. et al., "Molecular Cloning—A Laboratory Manual", Cold Spring Harbor Laboratory, NY, 1989). For example, it may be carried out by separating a fraction corresponding to the plasmid DNA from cells and cutting out the cDNA region from the plasmid DNA.

In the chemical synthesis method of the item (3), the polynucleotide of the present invention may be produced, for example, by binding DNA fragments produced by a chemical synthesis method. Each DNA can be synthesized using a DNA synthesizer [for example, Oligo 1000M DNA Synthesizer (Beckman) or 394 DNA/RNA Synthesizer (Applied Biosystems)].

Further, the polynucleotide of the present invention may be produced by nucleic acid chemical synthesis in accordance with a conventional method such as a phosphite triester method (Hunkapiller, M. et al., Nature, 10, 105–111, 1984), based on the information on the polypeptide of the present invention. In this connection, codons for each amino acid are known and can be optionally selected and determined by the conventional method, for example, by taking a codon usage of each host to be used into consideration (Crantham, R. et al., Nucleic Acids Res., 9, r43–r74, 1981). Further, a partial modification of codons of these base sequences can be carried out in accordance with a conventional method, such as site directed mutagenesis which uses a primer comprised of a synthetic oligonucleotide coding for a desired modification (Mark, D. F. et al., Proc. Natl. Acad. Sci. USA, 81, 5662–5666, 1984).

Determination of the DNA sequences obtained by the above-mentioned methods can be carried out by, for example, a Maxam-Gilbert chemical modification method (Maxam, A. M. and Gilbert, W., "Methods in Enzymology", 65, 499–559, 1980) or a dideoxynucleotide chain termination method (Messing, J. and Vieira, J., Gene, 19, 269–276, 1982).

[3] The Expression Vector and the Cell of the Present Invention

An isolated polynucleotide of the present invention is re-integrated into an appropriate vector DNA and a eucaryotic or procaryotic host cell may be transfected by the resulting expression vector. Further, it is possible to express the polynucleotide in a desired host cell, by introducing an appropriate promoter and a sequence related to the gene expression into the vector.

The expression vector of the present invention is not particularly limited, so long as it comprises the polynucleotide of the present invention. As the expression vector, there may be mentioned, for example, an expression vector obtained by introducing the polynucleotide of the present invention into a known expression vector appropriately selected in accordance with a host cell to be used.

The cell of the present invention is not particularly limited, so long as it is transfected with the expression vector of the present invention and comprises the polynucleotide of the present invention. The cell of the present invention may be, for example, a cell in which the polynucleotide is integrated into a chromosome of a host cell, or a cell containing the polynucleotide as an expression vector comprising polynucleotide. Further, the cell of the present invention may be a cell expressing the polypeptide of the present invention, or a cell not expressing the polypeptide of the present invention. The cell of the present invention may be obtained by, for example, transfecting a desired host cell with the expression vector of the present invention.

In the eucaryotic host cells, for example, cells of vertebrates, insects, and yeast are included. As the vertebral cell, there may be mentioned, for example, a simian COS cell (Gluzman, Y., Cell, 23, 175–182, 1981), a dihydrofolate reductase defective strain of a Chinese hamster ovary cell (CHO) (Urlaub, G. and Chasin, L. A., Proc. Natl. Acad. Sci. USA, 77, 4216–4220, 1980), a human embryonic kidney derived HEK293 cell, or a 293-EBNA cell (Invitrogen) obtained by introducing an EBNA-1 gene of Epstein Barr Virus into HEK293 cell.

As an expression vector for a vertebral cell, a vector containing a promoter positioned upstream of the gene to be expressed, an RNA splicing site, a polyadenylation site, a transcription termination sequence, and the like may be generally used. The vector may further contain a replication origin, if necessary. As the expression vector, there may be mentioned, for example, pSV2dhfr containing an SV40 early promoter (Subramani, S. et al., Mol. Cell. Biol., 1, 854–864, 1981), PEF-BOS containing a human elongation factor promoter (Mizushima, S. and Nagata, S., Nucleic Acids Res., 18, 5322, 1990), or pCEP4 containing a cytomegalovirus promoter (Invitrogen).

When the 293-EBNA cell is used as the host cell, for example, pCEP4 (Invitrogen) containing a replication origin of Epstein Barr Virus and capable of performing an autonomous replication in the 293-EBNA cell may be used as the expression vector.

When the COS cell is used as the host cell, a vector which has an SV40 replication origin, can perform an autonomous replication in the COS cell, and has a transcription promoter, a transcription termination signal, and an RNA splicing site, may be used as the expression vector. As the vector, there may be mentioned, for example, PME18S (Maruyama, K. and Takebe, Y., Med. Immunol., 20, 27–32, 1990), pEF-BOS (Mizushima, S. and Nagata, S., Nucleic Acids Res., 18, 5322, 1990), or pCDM8 (Seed, B., Nature, 329, 840–842, 1987).

The expression vector may be incorporated into COS cells by, for example, a DEAE-dextran method (Luthman, H. and Magnusson, G., Nucleic Acids Res., 11, 1295–1308, 1983), a calcium phosphate-DNA co-precipitation method (Graham, F. L. and van der Ed, A. J., Virology, 52, 456–457, 1973), a method using a commercially available transfection reagent (for example, FuGENE™6 Transfection Reagent; Boeringer Mannheim), or an electroporation method (Neumann, E. et al., EMBO J., 1, 841–845, 1982).

When the CHO cell is used as the host cell, a transfected cell capable of stably producing the polypeptide of the present invention can be obtained by carrying out co-transfection of an expression vector comprising the polynucleotide encoding the polypeptide of the present invention, together with a vector capable of expressing a neo gene which functions as a G418 resistance marker, such as pRSVneo (Sambrook, J. et al., "Molecular Cloning—A Laboratory Manual", Cold Spring Harbor Laboratory, NY, 1989) or pSV2-neo (Southern, P. J. and Berg, P., J. Mol. Appl. Genet., 1, 327–341, 1982), and selecting a G418 resistant colony.

The cell of the present invention may be cultured in accordance with the conventional method [for example,. "Shin Seikagaku Jikken Koza 18, Saibou Baiyou Gijyutsu (Japanese Biochemical Society)", Tokyo Kagaku Dojin, 1990], and the polypeptide of the present invention is produced outside the cells. As a medium to be used in the culturing, a medium commonly used in a desired host cell may be appropriately selected. In the case of the COS cell, for example, a medium such as an RPMI-1640 medium or a Dulbecco's modified Eagle's minimum essential medium (DMEM) may be used, by supplementing it with a serum component such as fetal bovine serum (FBS) if necessary. In the case of the 293-EBNA cell, a medium such as a Dulbecco's modified Eagle's minimum essential medium (DMEM) with a serum component such as fetal bovine serum (FBS) and G418 may be used.

The polypeptide of the present invention produced outside the cell of the present invention by culturing the cells may be separated and purified therefrom by various known separation techniques [for example, Okada, M. and Miyazaki K., "Kaitei, Tanpakushitsu Jikken Noto, Jyo•Ge (Revision, Notebook for Protein Experiments)", Yodo-sha 1999] making use of the physical properties, chemical properties and the like of the polypeptide. More particularly, the polypeptide of the present invention may be purified by treating a culture liquid containing the polypeptide of the present invention with a commonly used treatment, for example, a treatment with a protein precipitant, ultrafiltration, various liquid chromatography techniques such as molecular sieve chromatography (gel filtration), adsorption chromatography, ion exchange chromatography, affinity chromatography, or high performance liquid chromatography (HPLC), or dialysis, or a combination thereof.

When the polypeptide of the present invention is expressed as a fusion protein with a marker sequence in frame, identification of the expression of the polypeptide of the present invention, purification thereof, or the like may be easily carried out. As the marker sequence, there may be mentioned, for example, a FLAG tag, a hexa-histidine tag, a hemagglutinin tag, or a myc epitope. Further, by inserting a specific amino acid sequence recognized by a protease such as enterokinase, factor Xa, or thrombin between the marker sequence and the polypeptide of the present invention, the marker sequence may be removed by the protease.

[4] The Detecting Method and the Screening Method of the Present Invention

It is possible to detect whether or not a compound to be tested inhibits the aggrecanase activity of the polypeptide of the present invention, using the polypeptide of the present invention. Further, using this detecting method of the present invention, it is possible to screen a substance inhibiting the aggrecanase activity of the polypeptide of the present invention. The polypeptide of the present invention is a protein of which an expression is induced by differentiation to cartilage cells as described in Example 5, and the gene thereof is located in a chromosome relating to osteoarthritis (OA) as described in Example 6, and thus it is considered that the polypeptide of the present invention is an aggrecanase causative of joint diseases. Therefore, a substance inhibiting the aggrecanase activity of the polypeptide of the present invention is useful as a substance for treating joint diseases. Further, the polypeptide of the present invention per se may be used as a tool for screening a substance inhibiting the aggrecanase activity of the polypeptide of the present invention or a substance for treating joint diseases (particularly an agent for treating osteoarthritis).

Compounds to be tested which may be applied to the detecting method or screening method of the present invention are not particularly limited, but there may be mentioned, for example, various known compounds (including peptides) registered in chemical files, compounds obtained by combinatorial chemistry techniques (Terrett, N. K. et al., Tetrahedron, 51, 8135–8137, 1995) or conventional synthesis techniques, or random peptides prepared by employing a phage display method (Felici, F. et al., J. Mol. Biol., 222, 301–310, 1991) or the like. These known compounds include compounds (including peptides) known to exhibit an activity inhibiting metalloprotease but not known to inhibit the aggrecanase activity of the polypeptide of the present invention. In addition, culture supernatants of microorganisms, natural components derived from plants or marine organisms, or animal tissue extracts may be used as the test compounds for screening. Further, compounds (including peptides) obtained by chemically or biologically modifying compounds (including peptides) selected by the screening method of the present invention may be used.

The detecting method of the present invention may be carried out by a method similar to the above-mentioned method for confirming the aggrecanase activity, except that the polypeptide of the present invention, the substrate polypeptide, and the test compound are brought into contact with each other instead of bringing the test polypeptide into contact with the substrate polypeptide. Namely, in the detecting method of the present invention, it is possible to detect whether or not the test compound inhibits the aggrecanase activity of the polypeptide of the present invention by bringing the polypeptide of the present invention, the substrate polypeptide, and the test polypeptide into contact with each other and analyzing whether or not the substrate polypeptide is digested by the aggrecanase activity of the polypeptide of the present invention in the presence of the test compound (or analyzing the degree of the digestion). When the substrate polypeptide is not digested by the aggrecanase activity of the polypeptide of the present invention or the degree of the digestion is decreased, it is possible to confirm that the test compound inhibits the aggrecanase activity of the polypeptide of the present invention.

As the substrate polypeptide which may be used in the detecting method of the present invention, the substrate polypeptide previously described in the method for confirming the aggrecanase activity may be used.

In the detecting method of the present invention, as a method for analyzing whether or not the substrate polypeptide is digested by the aggrecanase activity of the polypeptide of the present invention, the methods previously described in the method for confirming the aggrecanase activity may be used. As these methods, there may be mentioned, for example, a method for analyzing a polypeptide fragment generated by digesting the substrate polypeptide by the aggrecanase activity of the polypeptide of the present invention (such as a method for detecting the presence of the polypeptide fragment, or a method for measuring an amount of the generated polypeptide fragment), or a method for analyzing the substrate polypeptide decreased by the digestion (such as a method for detecting the presence of the substrate polypeptide, or a method for measuring an amount of the decreased substrate polypeptide).

In the screening method of the present invention, it is possible to select a substance inhibiting the aggrecanase activity of the polypeptide of the present invention or a substance for treating joint diseases, on the basis of the results obtained by detecting whether or not the test compound inhibits the aggrecanase activity of the polypeptide of the present invention using the detecting method of the present invention. More particularly, for example, when the polypeptide of the present invention, the substrate polypeptide, and the test polypeptide are brought into contact with each other, a substance inhibiting the aggrecanase activity of the polypeptide of the present invention or a substance for treating joint diseases may be selected on the basis of the presence or degree of digestion of the substrate polypeptide in the presence of the test compound. When the substrate polypeptide is not digested by the aggrecanase activity of the polypeptide of the present invention or the degree of the digestion is decreased, it is possible to confirm that the test compound is a substance inhibiting the aggrecanase activity of the polypeptide of the present invention or a substance for treating joint diseases.

[5] The Process for Manufacturing a Pharmaceutical Composition for Treating Joint Diseases of the Present Invention The present invention includes a pharmaceutical composition for treating joint diseases comprising, as an active ingredient, a substance inhibiting the aggrecanase activity of the polypeptide of the present invention selected by the screening method of the present invention.

The present invention includes a process for manufacturing a pharmaceutical composition for treating joint diseases comprising the steps of detecting, in a quality control test of a pharmaceutical composition for treating joint diseases, whether or not the pharmaceutical composition inhibits the aggrecanase activity of the polypeptide of the present invention by the detecting method of the present invention, and preparing a medicament.

Further, the present invention includes a process for manufacturing a pharmaceutical composition for treating joint diseases, consisting of the step of preparing a medicament using a substance obtained by the screening method of the present invention comprising the detecting step.

The preparation containing as an active ingredient a substance inhibiting the aggrecanase activity of the polypeptide of the present invention may be prepared using carriers, fillers, and/or other additives generally used in the preparation of medicaments, in accordance with the active ingredient.

Examples of administration include oral administration by tablets, pills, capsules, granules, fine granules, powders, oral solutions and the like, and parenteral administration by injections (e.g., intravenous, intramuscular, or the like), suppositories, transdermal preparations, transmucosal absorption preparations and the like. Particularly, in the case of peptides which are digested in the stomach, a parenteral administration such as intravenous injection or the like, or preparation techniques in which the polypeptide is not digested, such as a preparation technique disclosed in the WO95/28963 pamphlet, is preferable.

In the solid composition for use in the oral administration, one or more active substances may be mixed with at least one inert diluent such as lactose, mannitol, glucose, microcrystalline cellulose, hydroxypropylcellulose, starch, polyvinyl pyrrolidone, or aluminum magnesium silicate. In the usual way, the composition may contain additives other than the inert diluent, such as a lubricant, a disintegrating agent, a stabilizing agent, or a solubilizing or solubilization assisting agent. If necessary, tablets or pills may be coated with a sugar coating or a film of a gastric or enteric substance.

The liquid composition for oral administration may include, for example, emulsions, solutions, suspensions, syrups, and elixirs, and may contain a generally used inert diluent such as purified water or ethyl alcohol. The composition may contain additives other than the inert diluent, such as moistening agents, suspending agents, sweeteners, flavors, or antiseptics.

The injections for parenteral administration may include aseptic aqueous or non-aqueous solutions, suspensions, and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil), alcohols (e.g., ethanol), polysorbate 80 and the like. Such a composition may further contain a moistening agent, an emulsifying agent, a dispersing agent, a stabilizing agent, a solubilizing or solubilization assisting agent, an antiseptic or the like. These compositions may be sterilized, for example, by filtration through a bacteria retaining filter, blending of a germicide, or irradiation. Alternatively, they may be used by first making into sterile solid compositions and dissolving them in sterile water or other sterile solvent for injection use prior to their use.

The dose is optionally decided by taking into consideration the strength of each active ingredient selected by the aforementioned screening method, or symptoms, age, sex, or the like of each patient to be administered.

For example, in the case of oral administration, the usual dosage, for an adult (60 kg in weight) is about 0.01 to 1000 mg, preferably 0.01 to 100 mg per day. In the case of parenteral administration, the usual dosage is about 0.01 to 1000 mg, preferably 0.01 to 100 mg per day in the form of an injection.

[6] The Antibody and the Fragment Thereof of the Present Invention

An antibody, such as a polyclonal antibody or a monoclonal antibody, which reacts with the polypeptide of the present invention may be obtained by directly administering the polypeptide of the present invention or a fragment thereof to various animals. Alternatively, it may be obtained by a DNA vaccine method (Raz, E. et al., Proc. Natl. Acad. Sci. USA, 91, 9519–9523, 1994; or Donnelly, J. J. et al., J. Infect. Dis., 173, 314–320, 1996), using a plasmid into which a polynucleotide encoding the polypeptide of the present invention is inserted.

The polyclonal antibody may be produced from a serum or eggs of an animal such as a rabbit, a rat, a goat, or a chicken, in which the animal is immunized and sensitized by the polypeptide of the present invention or a fragment thereof emulsified in an appropriate adjuvant (for example, Freund's complete adjuvant) by intraperitoneal, subcutaneous, or intravenous administration. The polyclonal antibody may be separated and purified from the resulting serum or eggs in accordance with conventional methods for polypeptide isolation and purification. Examples of the separation and purification methods include, for example, centrifugal separation, dialysis, salting-out with ammonium sulfate, or a chromatographic technique using such as DEAE-cellulose, hydroxyapatite, protein A agarose, and the like.

The monoclonal antibody may be easily produced by those skilled in the art, according to, for example, a cell fusion method of Kohler and Milstein (Kohler, G. and Milstein, C., Nature, 256, 495–497, 1975).

A mouse is immunized intraperitoneally, subcutaneously, or intravenously several times at an interval of a few weeks by a repeated inoculation of emulsions in which the polypeptide of the present invention or a fragment thereof is emulsified into a suitable adjuvant such as Freund's complete adjuvant. Spleen cells are removed after the final immunization, and then fused with myeloma cells to prepare hybridomas.

As a myeloma cell for obtaining a hybridoma, a myeloma cell having a marker such as a deficiency in hypoxanthine-guanine phosphoribosyltransferase or thymidine kinase (for example, mouse myeloma cell line P3X63Ag8.U1) may be used. As a fusing agent, polyethylene glycol may be used. As a medium for preparation of hybridomas, for example, a commonly used medium such as an Eagle's minimum essential medium, a Dulbecco's modified minimum essential medium, or an RPMI-1640 medium may be used by adding properly 10 to 30% of a fetal bovine serum. The fused strains may be selected by a HAT selection method. A culture supernatant of the hybridomas is screened by a well-known method such as an ELISA method or an immunohistological method, to select hybridoma clones secreting the antibody of interest. The monoclonality of the selected hybridoma is guaranteed by repeating subcloning by a limiting dilution method. Antibodies in an amount which may be purified are produced by culturing the resulting hybridomas in a medium for 2 to 4 days, or in the peritoneal cavity of a pristane-pretreated BALB/c strain mouse for 10 to 20 days.

The resulting monoclonal antibodies in the culture supernatant or the ascites may be separated and purified by conventional polypeptide isolation and purification methods. Examples of the separation and purification methods include, for example, centrifugal separation, dialysis, salting-out with ammonium sulfate, or chromatographic technique using such as DEAE-cellulose, hydroxyapatite, protein A agarose, and the like.

Further, the monoclonal antibodies or the antibody fragments containing a part thereof may be produced by inserting the whole or a part of a gene encoding the monoclonal antibody into an expression vector and introducing the resulting expression vector into appropriate host cells (such as *E. coli*, yeast, or animal cells)

Antibody fragments comprising an active part of the antibody such as F(ab')$_2$, Fab, Fab', or Fv may be obtained by a conventional method, for example, by digesting the separated and purified antibodies (including polyclonal antibodies and monoclonal antibodies) with a protease such as pepsin or papain, and separating and purifying the resulting fragments by standard polypeptide isolation and purification methods.

Further, an antibody which reacts to the polypeptide of the present invention may be obtained in a form of single chain Fv or Fab in accordance with a method of Clackson et al. or a method of Zebedee et al. (Clackson, T. et al., Nature, 352, 624–628, 1991; or Zebedee, S. et al., Proc. Natl. Acad. Sci. USA, 89, 3175–3179, 1992). Furthermore, a humanized antibody may be obtained by immunizing a transgenic mouse in which mouse antibody genes are substituted with human antibody genes (Lonberg, N. et al., Nature, 368, 856–859, 1994).

EXAMPLES

The present invention now will be further illustrated by, but is by no means limited to, the following Examples. The procedures were performed in accordance with the known

Example 1

Preparation of Expression Vector Having FLAG Added to C-terminus

A expression vector pCEP4d wherein the Estein-Barr virus EBNA1 expression unit was removed is constructed by digesting plasmid pCEP4 (manufactured by Invitrogen) with restriction enzymes ClaI and NsiI, blunt-ending and then self-ligating. The resulting expression vector. pCEP4d was digested with restriction enzymes, NheI and BamHI, and the resulting DNA fragment of approximately 7.7 kbp was extracted from agalose gel, then to which the double stranded oligonucleotide prepared by annealing the oligonucleotide consisting of the base sequence of SEQ ID NO: 7 and the oligonucleotide consisting of the base sequence of SEQ ID NO: 8 was inserted to construct the expression vector pCEP4d-FLAG. The base sequence of the resulting expression vector was analyzed to confirm that the desired sequence was included therein.

A PCR was carried out, using the expression vector pCEP4d-FLAG as a template, the oligonucleotide consisting of the base sequence of SEQ ID NO: 9 and the oligonucleotide consisting of the base sequence of SEQ ID NO: 10 as primers, and PyroBest DNA polymerase (PyroBest™; manufactured by Takara-shuzo). In the PCR, a thermal denaturing reaction was performed first at 94° C. for 2 minutes. Then, a cycle reaction composed of treatments at 94° C. for 30 seconds, at 55° C. for 30 seconds and at 72° C. for 30 seconds was repeated 15 times. Thereafter, an extension reaction was carried out at 72° C. for 7 minutes.

A resulting DNA fragment of approximately 0.4 kbp was digested with a restriction enzyme, SpeI, and inserted into the expression vector pCEP4d-FLAG (about 7.7 kbp) which had been digested with XbaI, to obtain an expression vector pCEP4dE2-FLAG. In the resulting expression vector pCEP4dE2-FLAG, the XbaI recognition sequence, the NheI recognition sequence, the NotI recognition sequence, and the BamHI recognition sequence, and the FLAG tag were arranged from the promoter to the downstream thereof.

Example 2

Cloning of Full-length ORF Gene of Novel Aggrecanase Gene MDTS8

A PCR was carried out, using a combination of the oligonucleotide consisting of the base sequence of SEQ ID NO: 3 (having an XbaI recognition sequence and a Kozak sequence added to the 5'-terminus) and the oligonucleotide consisting of the base sequence of SEQ ID NO: 4 (having an NotI recognition sequence added to the 5'-terminus) as the primers, a human placenta cDNA library (Marathon-Ready™ cDNA; manufactured by Clontech) as a template, and DNA polymerase (TaKaRa LA Taq™; manufactured by Takara-shuzo) as the DNA polymerase. In the PCR, a thermal denaturing reaction was first performed at 94° C. for 2 minutes. Then, a cycle composed of treatments at 98° C. for 10 seconds, and 68° C. for 3 minutes was repeated 45 times. Thereafter, an extension reaction was carried out at 68° C. for 7 minutes.

A resulting PCR product, a DNA fragment with approximately 2.3 kbp (having the XbaI recognition sequence and the Kozak sequence added to the 5'-terminus, and the NotI recognition sequence added to the 3'-terminus), was subcloned into a plasmid PCR2.1 (manufactured by Invitrogen) to obtain a clone pMDTS8Cys.

The resulting plasmid pMDTS8Cys was digested with restriction enzymes, XbaI and NotI, and a resulting DNA fragment of approximately 2.3 kbp was inserted into the XbaI and NotI site of the plasmid pCEP4dE2-FLAG constructed in Example 1 to obtain a plasmid pCEPdE2-MDTS8Cys-FLAG.

The resulting plasmid pCEPdE2-MDTS8Cys-FLAG was digested with restriction enzymes, KpnI and NotI, to obtain a DNA fragment of approximately 8.3 kbp (hereinafter referred to as DNA Fragment A). Further, the resulting plasmid pCEPdE2-MDTS8Cys-FLAG was digested with restriction enzymes, KpnI and SpeI, to obtain a DNA fragment of approximately 1.5 kbp (hereinafter referred to as DNA Fragment B).

The procedures described as above were repeated except that a combination of the oligonucleotide consisting of the base sequence of SEQ ID NO: 5 and the oligonucleotide consisting of the base sequence of SEQ ID NO: 6 (having an NotI recognition sequence added to the 5'-terminus) was used as the primers, instead of the combination of the oligonucleotide consisting of the base sequence of SEQ ID NO: 3 and the oligonucleotide consisting of the base sequence of SEQ ID NO: 4. A resulting PCR product, a DNA fragment of approximately 1.5 kbp (having the NotI recognition sequence added to the 3'-terminus), was subcloned into the plasmid PCR2.1 (manufactured by Invitrogen) to obtain a clone pMDTS8-3H. The resulting clone pMDTS8-3H was digested with restriction enzymes, SpeI and NotI, to obtain a DNA fragment with about 1.5 kbp (hereinafter referred to as DNA Fragment C).

The above DNA Fragment A, the above DNA Fragment B. and the above DNA Fragment C were ligated to prepare a plasmid pCEPdE2-MDTS8Full-FLAG. The resulting plasmid pCEPdE2-MDTS8Full-FLAG contains a gene consisting of a 1st to 3663rd bases in the base sequence of SEQ ID NO: 1, i.e., the base sequence of the novel aggrecanase gene MDTS8. A polypeptide having a 1st to 1221st amino acid sequence in the amino acid sequence of SEQ ID NO: 2 and an amino acid sequence of SEQ ID NO: 23 added to the C-terminus thereof can be expressed from an animal cell as a host.

Example 3

Expression of MDTS8 Full-length Protein (MDTS8Full)

A commercially available transfection reagent (Fu-GENE™6 Transfection Reagent; manufactured by Boehringer Mannheim) was used, in accordance with a protocol attached thereto, to introduce the plasmid pCEPdE2-MDTS8Full-FLAG prepared in Example 2, or the plasmid pCEP4dE2-FLAG as a control, into an HEK293-EBNA cell manufactured by Invitrogen.

An existence of the desired protein in a supernatant of a culture obtained 1 day to 2 days after the introduction of the plasmid was confirmed by a western blotting using an antibody (mouse anti-FLAG monoclonal antibody M2; manufactured by Sigma) against the FLAG tag added to the C-terminus. More particularly, the culture supernatant was electrophoresed on an SDS/10%–20% acrylamide gel; manufactured by Daiichi Pure Chemicals, and transferred to a polyvinylidene difluoride (PVDF) membrane by a blotting apparatus. To the resulting PVDF membrane, a blocking agent (Block-ace manufactured by Dainippon Pharmaceutical) was added to perform a blocking. Then, the products on the membrane were reacted successively with the mouse anti-FLAG monoclonal antibody M2 and a rabbit anti-mouse IgG polyclonal antibody labeled with horseradish peroxidase (manufactured by Zymed or TAGO). Alternatively, after blocking, the products on the membrane were reacted successively with a biotinylated antibody M2 (manufactured by Sigma) and a streptoavidin labeled with horseradish peroxidase (manufactured by Amersham Pharmacia Biotech). After the reaction, an expression of the desired protein was confirmed by a commercially available western blotting detecting system (ECL Western Blotting Detecting System; manufactured by Amersham Pharmacia Biotech).

An apparent molecular weight of the detected protein on the SDS-polyacrylamide gel electrophoresis (SDS-PAGE) was about 120 to 140 kDa.

Example 4

Confirmation of Aggrecanase Activity of MDTS8 Full-length Protein (1) Preparation of Recombinant Aggrecan G1G2

A PCR was carried out, using a combination of the oligonucleotide consisting of the base sequence of SEQ ID NO: 11 prepared on the basis of the gene sequence of a known human aggrecan (Doege K., et al., Biochem. Soc. Trans., 18, 200–202, 1990) and the oligonucleotide consisting of the base sequence of SEQ ID NO: 12 as the primers, a human placenta cDNA library (Marathon-Ready™ cDNA; manufactured by Clontech) as a template, and a PyroBest™ DNA polymerase (manufactured by Takara-shuzo) as the DNA polymerase. In the PCR, a thermal denaturing reaction was first performed at 94° C. for 1 minute. Then, a cycle composed of treatments at 98° C. for 10 seconds, and 68° C. for 2 minutes was repeated 40 times. Thereafter, an extension reaction was carried out at 68° C. for 7 minutes.

A resulting PCR product, a DNA fragment, was digested with a restriction enzyme, BamHI, and a resulting DNA fragment was inserted into the BamHI site of the plasmid pCEP-SigFla to prepare an expression plasmid pCEP-rAgg for expressing a protein (hereinafter referred to as a recombinant G1G2) containing a globular domain 1—globular domain 2 of the human aggrecan and an FLAG tag added to the N-terminus of the globular domain 1—the globular domain 2 and His tag added to the C-terminus of the globular domain 1—the globular domain 2. The plasmid pCEP-SigFla was an expression vector prepared by inserting a double-stranded oligonucleotide which had been prepared by annealing the oligonucleotide consisting of the base sequence of SEQ ID NO: 13 and the oligonucleotide consisting of the base sequence of SEQ ID NO: 14, into the HindIII and XhoI site of the plasmid pCEP4d prepared in Example 1. The plasmid pCEP-SigFla contained a secretory signal sequence (Guan X-M., et al., J. Biol. Chem., 267, 21995–21998, 1992) stemmed from hemaglutinin of an influenza virus, a FLAG tag sequence, and a BamHI recognition sequence, in the order as above, from the promoter to the downstream thereof.

A resulting expression plasmid DCEP-rAgg was introduced into the HEK293-EBNA cell, and the transformant was cultured for 3 to 7 days to express the desired protein, i.e., the recombinant aggrecan G1G2. The desired protein was purified from the culture supernatant by an affinity chromatography, making use of the FLAG tag attached to the N-terminus. More particularly, the culture supernatant was applied to M2-agalose (manufactured by Sigma) packed in a column, washed with 20 mmol/L tris-HCl (pH 7.4)/150 mmol/L sodium chloride (hereinafter referred to as TBS), eluted by 0.1 mol/L glycine hydrochloride (pH 3.0) to fractionate, and immediately neutralized with 1 mmol/L tris-HCl (pH 8.0).

(2) Detection of Aggrecanase Activity

As described in Example 3, the plasmid PCEPdE2-MDTS8Full-FLAG prepared in Example 2 of the plasmid pCEPdE2-FLAG prepared in Example 1 as a control was introduced into an HEK293-EBNA cell (manufactured by Invitrogen). Then, 16 hours after the plasmid introduction, a medium was replaced with a serum-free medium. The cultivation was continued for 34 hours, and thereafter a culture supernatant was recovered.

The resulting culture supernatant was mixed with the recombinant G1G2 prepared in Example 4(1), and reacted at 37° C. overnight. Thereafter, as described in Example 3, an SDS-PAGE, a transfer to a PVDF membrane, and a blocking were carried out. Then, the products on the PVDF membrane were reacted successively with the mouse monoclonal antibody BC-3 (Hughes C. E., et al., Biochemical J., 305, 799–804, 1995) capable of recognizing an aggrecanase neo-epitope, and a goat anti-mouse IgG polyclonal antibody labeled with peroxidase (manufactured by TAGO). Then, a western blotting detecting system (ECL Western Blotting Detecting System; manufactured by Amersham Pharmacia) was used for detection.

It was revealed that, when the culture supernatant of the HEK293-EBNA cell transfected with the plasmid pCEPdE2-FLAG (control) was reacted with the recombinant G1G2, no degradation product reactive with the anti-aggrecanase neo-epitope antibody was detected, whereas such degradation products were detected when the culture supernatant of the HEK293-EBNA cell transfected with the plasmid pCEPdE2-MDTS8Full-FLAG was reacted with the recombinant G1G2.

The present Example shows that MDTS8 has an aggrecanase activity.

Example 5

Induction of MDTS8 mRNA Expression, Accompanied by Differentiation to Cartilage Cell (1) Differentiation Induction from Mesenchymal Stem Cells to Cartilage Cell It is known that a human mesenchymal stem cell is differentiated to a cartilage cell when cultivated under spheroid pellet with a stimulation of TGF-β3 or the like (Pittenger M. F., et al., Science, 284, 143–147, 1999).

Normal human mesenchymal stem cells (manufactured by Bio Whittaker) were cultured in a human mesenchymal stem cells proliferation medium kit (manufactured by Bio Whittaker) to obtain 5×10$^5$ cells. Then, 2.5×10$^5$ cells were washed with an incomplete chondrogenesis induction medium [DMEM-high glucose (manufactured by LIFE TECHNOLOGIES), 1 mmol/L-sodium pyruvate (manufactured by LIFE TECHNOLOGIES), 0.35 mmol/L-proline (manufactured by LIFE TECHNOLOGIES), 0.1 μmol/L-dexamethasone (manufactured by Sigma), 0.17 mmol/L-ascorbic acid 2-phosphate (manufactured by Sigma), and ITS+1 Culture Supplement (manufactured by Sigma)], and suspended in 500 μL of a complete chondrogenesis induction medium [an incomplete cartilage differentiation induction medium containing 0.01 μg/mL TGF-β3 (manufactured by Sigma)]. Then, the suspension was transferred into a polypropylene tube and centrifuged at 150×g for 5 minutes to obtain a cell pellet. The resulting cell pellet was placed in a cell cultivating apparatus as it was, and cultivated. The cultivation was continued for 2 weeks while the medium was changed to a complete cartilage differentiation induction medium every 3 or 4 days, so that the cells were differentiated to cartilage cells.

(2) Confirmation of Differentiation to Cartilage Cells

A total RNA was prepared from each of undifferentiated human mesenchymal stem cells and cells induced to differentiation, by a commercially available total RNA purifying reagent (ISOGEN; manufactured by Nippon Gene). The resulting total RNA was reacted with DNase (manufactured by Nippon Gene) at 37° C. for 15 minutes. The resulting DNase-treated total RNA (0.5 μg) was converted to cDNA by a Superscript first-strand system (for RT-PCR; manufactured by LIFE TECHNOLOGIES).

The differentiation from the human mesenchymal stem cells to cartilage cells by the differentiation induction treatment as disclosed in Example 5(1) was confirmed by a remarkable increase of an expression of mRNAs of collagen type II and collagen type IX specifically expressed in cartilage cells, with the differentiation induction proceeded. More particularly, a quantitative PCR using a sequence detector (Prism7700 Sequence Detector; manufactured by Applied Biosystems) was used to measure an existing amount and make a comparison. For collagen type II, a combination of the oligonucleotide consisting of the base sequence of SEQ ID NO: 15 and the oligonucleotide consisting of the base sequence of SEQ ID NO: 16 was used as a primer set, and for collagen type IX, a combination of the oligonucleotide consisting of the base sequence of SEQ ID NO: 17 and the oligonucleotide consisting of the base sequence of SEQ ID NO: 18 was used as a primer set. A commercially available PCR agent (SYBR Green PCR core reagent; manufactured by Applied Biosystems) was used to perform the PCR. In the PCR, an initial denaturing reaction was performed at 95° C. for 10 minutes. Then, a cycle reaction composed of treatments at 94° C. for 15 seconds, at 60° C. for 30 seconds and 72° C. for 60 seconds was repeated 45 times.

Further, a PCR was carried out, using human genome DNA as a template and the primer set as above under the same conditions, to obtain a standard curve for calculating an amount of mRNA expressed. A PCR was carried out, using the cDNA as above and human genome DNA as templates and the oligonucleotide consisting of the base sequence of SEQ ID NO: 21 and the oligonucleotide consisting of the base sequence of SEQ ID NO: 22 as the primer set under the same conditions to calculate an amount of human glyceraldehyde-3-phosphate dehydrogenase (g3pdh) expressed, as an internal standard. The existing amounts of mRNAs of collagen type II and collagen type IX were amended on the basis of the determined values of G3PDH.

(3) Expression of MDTS8 Gene in Cartilage Cells

The oligonucleotide consisting of the base sequence of SEQ ID NO: 19 and the oligonucleotide consisting of the base sequence of SEQ ID NO: 20 were designed on the basis of the base sequence of SEQ ID NO: 1, as a primer set for measuring an amount of mRNA of the novel aggrecanase gene MDTS8. A PCR was carried out, using the above primer set, cDNA (corresponding to 5 ng of total RNA) prepared in Example 5(2) as a template, and a DNA polymerase (TaKaRa LA Taq™; manufactured by Takarashuzo). In the PCR, a thermal denaturing reaction was first performed at 94° C. for 2 minutes. Then, a cycle composed of treatments at 98° C. for 10 seconds, at 60 for 30 seconds, and 72° C. for 1 minute was repeated 40 times.

A PCR was carried out to monitor the expression of the G3PDH gene, using a combination of the oligonucleotide consisting of the base sequence of SEQ ID NO: 21 and the oligonucleotide consisting of the base sequence of SEQ ID NO: 22 as a primer set, cDNA (corresponding to 5 ng of total RNA) prepared in Example 5(2) as a template, and a DNA polymerase (TaKaRa LA Taq™; manufactured by Takarashuzo). In the PCR, a thermal denaturing reaction was first performed at 94° C. for 2 minutes. Then, a cycle composed of treatments at 98° C. for 10 seconds, at 60° C. for 30 seconds, and 72° C. for 1 minute was repeated 30 times.

It was revealed that a substantial change of the expression of G3PDH gene, accompanied by the differentiation to cartilage cells, was not observed, whereas mRNA of the novel aggrecanase gene MDTS8 of the present invention was not detected in the human mesenchymal stem cells before differentiation, but was detected as a band of about 0.33 kbp in the cartilage cells. This shows that mRNA of the novel aggrecanase gene MDTS8 of the present invention is expressed in cartilage cells.

Example 6

Chromosome Mapping of Novel Aggrecanase Gene MDTS8

A BLAST search was conducted on the GenBank for the gene sequence of the full-length ORF of the novel aggrecanase gene consisting of the base sequence of SEQ ID NO: 1 of the present invention as an inquiry sequence. It was found that BAC clones AC026498, AC025284, AC010548, and AC009139 contain partial sequences of the MDTS8, and a part of at least 24 exons is present in each of the clones.

Then, it was confirmed that the four clones as above are located on the chromosome 16q, by the public database (Human Genome Reconstruction Project; http://hgrep.ims.u-tokyo.ac.jp/cgi-bin/HTG_tool/view.cgi?layer=top) established by The Institute of Medical Science, The University of Tokyo and RIKEN and published on the web. Further, it was also confirmed that the four clones as above contain gene markers WI-22533, stSG3069, SGC32952, and stSG62732 which are located on the chromosome 16q.

Subsequently, more detailed chromosome mapping was conducted, using the markers WI-22533, stSG3069, SGC32952, and stSG62732 located on the chromosome 16q. More particularly, the above four gene markers were searched for in another public database (The Genome Database; http://www.gdb.org/). It was found that each of the four markers were located on 16q22.3–23.1 of the physical map of chromosomes, and thus, the MDTS8 is located on 16q22.3–23.1. Therefore, it becomes apparent that the chromosomal position of MDTS8 belongs to a region specified as an OA-susceptibility locus, i.e., a joint disease.

INDUSTRIAL APPLICABILITY

The polypeptide of the present invention is a novel aggrecanase causative of joint diseases (particularly OA), and thus a substance inhibiting the aggrecanase activity of the polypeptide of the present invention is useful as a substance for treating joint diseases.

According to the polypeptide of the present invention, a convenient screening system for an agent for treating joint diseases can be provided. Namely, by the detecting method of the present invention using the polypeptide of the present invention, a substance for treating joint diseases can be screened by selecting a substance inhibiting the aggrecanase activity of the polypeptide of the present invention.

Further, a pharmaceutical composition for treating joint diseases can be produced by preparing a medicament using a substance selected by the screening method, as an active ingredient, and a carrier, a filler, and/or other additives.

The detecting method of the present method can be used not only for screening a substance for treating joint diseases but also for a quality control test of a pharmaceutical composition for treating joint diseases. Namely, a pharmaceutical composition for treating joint diseases can be produced by detecting whether or not a compound to be tested inhibits the aggrecanase activity of the polypeptide of the present invention, by the detecting method of the present invention, and then preparing a medicament using the resulting substance inhibiting the aggrecanase activity.

Further, the polynucleotide, the expression vector, the cell, and the antibody of the present invention are useful for producing the polypeptide of the present invention Free Text in Sequence Listing Features of "Artificial Sequence" are described in the numeric identifier <223> in the Sequence Listing. More particularly, each of the base sequences of SEQ ID NOS: 3–6 and 9–12 is an artificially synthesized primer sequence. Each of the base sequences of SEQ ID NOS: 7, 8, 13, and 14 is an artificially synthesized linker sequence. The base sequence of SEQ ID NO: 23 is an artificially synthesized sequence containing a restriction enzyme NotI recognition sequence and a FLAG tag sequence.

As above, the present invention is explained with reference to particular embodiments, but modifications and improvements obvious to those skilled in the art are included in the scope of the present invention.

The invention claimed is:

1. An isolated polynucleotide comprising a nucleotide sequence encoding a polypeptide selected from:
   a) a polypeptide consisting of the amino acid sequence of SEQ ID NO: 2;
   b) a polypeptide comprising the amino acid sequence of SEQ ID NO: 2; and
   c) a polypeptide comprising an amino acid sequence having 95% or more homology with the amino acid sequence of SEQ ID NO: 2, and exhibiting aggrecanase activity.

2. An expression vector comprising at least one of the polynucleotides according to claim 1.

3. A cell transfected with at least one of the expression vectors according to claim 2.

* * * * *

SEQUENCE LISTING

```
<160> NUMBER OF SEQ ID NOS: 26

<210> SEQ ID NO 1
<211> LENGTH: 3666
<212> TYPE: DNA
<213> ORGANISM: Homo sapiens
<220> FEATURE:
<221> NAME/KEY: CDS
<222> LOCATION: (1)..(3666)

<400> SEQUENCE: 1 atg gag tgc gcc ctc ctg ctc gcg tgt gcc ttc ccg gct gcg ggt tcg      48
Met Glu Cys Ala Leu Leu Leu Ala Cys Ala Phe Pro Ala Ala Gly Ser
 1               5                  10                  15 ggc ccg ccg agg ggc ctg gcg gga ctg ggg cgc gtg gcc aag gcg ctc      96
Gly Pro Pro Arg Gly Leu Ala Gly Leu Gly Arg Val Ala Lys Ala Leu
             20                  25                  30 cag ctg tgc tgc ctc tgc tgt gcg tcg gtc gcc gcg gcc tta gcc agt     144
Gln Leu Cys Cys Leu Cys Cys Ala Ser Val Ala Ala Ala Leu Ala Ser
         35                  40                  45 gac agc agc agc ggc gcc agc gga tta aat gat gat tac gtc ttt gtc     192
Asp Ser Ser Ser Gly Ala Ser Gly Leu Asn Asp Asp Tyr Val Phe Val
     50                  55                  60 acg cca gta gaa gta gac tca gcc ggg tca tat att tca cac gac att     240
Thr Pro Val Glu Val Asp Ser Ala Gly Ser Tyr Ile Ser His Asp Ile
 65                  70                  75                  80 ttg cac aac ggc agg aaa aag cga tcg gcg cag aat gcc aga agc tcc     288
Leu His Asn Gly Arg Lys Lys Arg Ser Ala Gln Asn Ala Arg Ser Ser
                 85                  90                  95 ctg cac tac cga ttt tca gca ttt gga cag gaa ctg cac tta gaa ctt     336
Leu His Tyr Arg Phe Ser Ala Phe Gly Gln Glu Leu His Leu Glu Leu
            100                 105                 110 aag ccc tcg gcg att ttg agc agt cac ttt att gtc cag gta ctt gga     384
Lys Pro Ser Ala Ile Leu Ser Ser His Phe Ile Val Gln Val Leu Gly
        115                 120                 125 aaa gat ggt gct tca gag act cag aaa ccc gag gtg cag caa tgc ttc     432
Lys Asp Gly Ala Ser Glu Thr Gln Lys Pro Glu Val Gln Gln Cys Phe
    130                 135                 140 tat cag gga ttt atc aga aat gac agc tcc tcc tct gtc gct gtg tct     480
```

-continued

```
            Tyr Gln Gly Phe Ile Arg Asn Asp Ser Ser Ser Val Ala Val Ser
            145                 150                 155                 160 acg tgt gct ggc ttg tca ggt tta ata agg aca cga aaa aat gaa ttc          528
Thr Cys Ala Gly Leu Ser Gly Leu Ile Arg Thr Arg Lys Asn Glu Phe
                165                 170                 175 ctc atc tcg cca tta cct cag ctt ctg gcc cag gaa cac aac tac agc          576
Leu Ile Ser Pro Leu Pro Gln Leu Leu Ala Gln Glu His Asn Tyr Ser
                180                 185                 190 tcc cct gcg ggt cac cat cct cac gta ctg tac aaa agg aca gca gag          624
Ser Pro Ala Gly His His Pro His Val Leu Tyr Lys Arg Thr Ala Glu
            195                 200                 205 gag aag atc cag cgg tac cgt ggc tac ccc ggc tct ggc cgg aat tat          672
Glu Lys Ile Gln Arg Tyr Arg Gly Tyr Pro Gly Ser Gly Arg Asn Tyr
        210                 215                 220 cct ggt tac tcc cca agt cac att ccc cat gca tct cag agt cga gag          720
Pro Gly Tyr Ser Pro Ser His Ile Pro His Ala Ser Gln Ser Arg Glu
225                 230                 235                 240 aca gag tat cac cat cga agg ttg caa aag cag cat ttt tgt gga cga          768
Thr Glu Tyr His His Arg Arg Leu Gln Lys Gln His Phe Cys Gly Arg
                245                 250                 255 cgc aag aaa tat gct ccc aag cct ccc aca gag gac acc tat cta agg          816
Arg Lys Lys Tyr Ala Pro Lys Pro Pro Thr Glu Asp Thr Tyr Leu Arg
                260                 265                 270 ttt gat gaa tat ggg agc tct ggg cga ccc aga aga tca gct gga aaa          864
Phe Asp Glu Tyr Gly Ser Ser Gly Arg Pro Arg Arg Ser Ala Gly Lys
            275                 280                 285 tca caa aag ggc ctc aat gtg gaa acc ctc gtg gtg gca gac aag aaa          912
Ser Gln Lys Gly Leu Asn Val Glu Thr Leu Val Val Ala Asp Lys Lys
        290                 295                 300 atg gtg gaa aag cat ggc aag gga aat gtc acc aca tac att ctc aca          960
Met Val Glu Lys His Gly Lys Gly Asn Val Thr Thr Tyr Ile Leu Thr
305                 310                 315                 320 gta atg aac atg gtt tct ggc cta ttt aaa gat ggg act att gga agt         1008
Val Met Asn Met Val Ser Gly Leu Phe Lys Asp Gly Thr Ile Gly Ser
                325                 330                 335 gac ata aac gtg gtt gtg gtg agc cta att ctt ctg gaa caa gaa cct         1056
Asp Ile Asn Val Val Val Val Ser Leu Ile Leu Leu Glu Gln Glu Pro
                340                 345                 350 gga gga tta ttg atc aac cat cat gca gac cag tct ctg aat agt ttt         1104
Gly Gly Leu Leu Ile Asn His His Ala Asp Gln Ser Leu Asn Ser Phe
            355                 360                 365 tgt caa tgg cag tct gcc ctc att gga aag aat ggc aag aga cat gat         1152
Cys Gln Trp Gln Ser Ala Leu Ile Gly Lys Asn Gly Lys Arg His Asp
        370                 375                 380 cat gcc atc tta cta aca gga ttt gat att tgt tct tgg aag aat gaa         1200
His Ala Ile Leu Leu Thr Gly Phe Asp Ile Cys Ser Trp Lys Asn Glu
385                 390                 395                 400 cca tgt gac act cta ggg ttt gcc ccc atc agt gga atg tgc tct aag         1248
Pro Cys Asp Thr Leu Gly Phe Ala Pro Ile Ser Gly Met Cys Ser Lys
                405                 410                 415 tac cga agt tgt acc atc aat gag gac aca gga ctt ggc ctt gcc ttc         1296
Tyr Arg Ser Cys Thr Ile Asn Glu Asp Thr Gly Leu Gly Leu Ala Phe
                420                 425                 430 acc atc gct cat gag tca ggg cac aac ttt ggt atg att cac gac gga         1344
Thr Ile Ala His Glu Ser Gly His Asn Phe Gly Met Ile His Asp Gly
            435                 440                 445 gaa ggg aat ccc tgc aga aag gct gaa ggc aat atc atg tct ccc aca         1392
Glu Gly Asn Pro Cys Arg Lys Ala Glu Gly Asn Ile Met Ser Pro Thr
        450                 455                 460
```

```
ctg acc gga aac aat gga gtg ttt tca tgg tct tcc tgc agc cgc cag        1440
Leu Thr Gly Asn Asn Gly Val Phe Ser Trp Ser Ser Cys Ser Arg Gln
465                 470                 475                 480 tat ctc aag aaa ttc ctc agc aca cct cag gcg ggg tgt cta gtg gat        1488
Tyr Leu Lys Lys Phe Leu Ser Thr Pro Gln Ala Gly Cys Leu Val Asp
                    485                 490                 495 gag ccc aag caa gca gga cag tat aaa tat ccg gac aaa cta cca gga        1536
Glu Pro Lys Gln Ala Gly Gln Tyr Lys Tyr Pro Asp Lys Leu Pro Gly
                500                 505                 510 cag att tat gat gct gac aca cag tgt aaa tgg caa ttt gga gca aaa        1584
Gln Ile Tyr Asp Ala Asp Thr Gln Cys Lys Trp Gln Phe Gly Ala Lys
            515                 520                 525 gcc aag tta tgc agc ctt ggt ttt gtg aag gat att tgc aaa tca ctt        1632
Ala Lys Leu Cys Ser Leu Gly Phe Val Lys Asp Ile Cys Lys Ser Leu
        530                 535                 540 tgg tgc cac cga gta ggc cac agg tgt gag acc aag ttt atg ccc gca        1680
Trp Cys His Arg Val Gly His Arg Cys Glu Thr Lys Phe Met Pro Ala
545                 550                 555                 560 gca gaa ggg acc gtt tgt ggc ttg agt atg tgg tgt cgg caa ggc cag        1728
Ala Glu Gly Thr Val Cys Gly Leu Ser Met Trp Cys Arg Gln Gly Gln
                565                 570                 575 tgc gta aag ttt ggg gag ctc ggg ccc cgg ccc atc cac ggc cag tgg        1776
Cys Val Lys Phe Gly Glu Leu Gly Pro Arg Pro Ile His Gly Gln Trp
                580                 585                 590 tcc gcc tgg tcg aag tgg tca gaa tgt tcc cgg aca tgt ggt gga gga        1824
Ser Ala Trp Ser Lys Trp Ser Glu Cys Ser Arg Thr Cys Gly Gly Gly
            595                 600                 605 gtc aag ttc cag gag aga cac tgc aat aac ccc aag cct cag tat ggt        1872
Val Lys Phe Gln Glu Arg His Cys Asn Asn Pro Lys Pro Gln Tyr Gly
        610                 615                 620 ggc tta ttc tgt cca ggt tct agc cgt att tat cag ctg tgc aat att        1920
Gly Leu Phe Cys Pro Gly Ser Ser Arg Ile Tyr Gln Leu Cys Asn Ile
625                 630                 635                 640 aac cct tgc aat gaa aat agc ttg gat ttt cgg gct caa cag tgt gca        1968
Asn Pro Cys Asn Glu Asn Ser Leu Asp Phe Arg Ala Gln Gln Cys Ala
                645                 650                 655 gaa tat aac agc aaa cct ttc cgt gga tgg ttc tac cag tgg aaa ccc        2016
Glu Tyr Asn Ser Lys Pro Phe Arg Gly Trp Phe Tyr Gln Trp Lys Pro
                660                 665                 670 tat aca aaa gtg gaa gag gaa gat cga tgc aaa ctg tac tgc aag gct        2064
Tyr Thr Lys Val Glu Glu Glu Asp Arg Cys Lys Leu Tyr Cys Lys Ala
            675                 680                 685 gag aac ttt gaa ttt ttt ttt gca atg tcc ggc aaa gtg aaa gat gga        2112
Glu Asn Phe Glu Phe Phe Phe Ala Met Ser Gly Lys Val Lys Asp Gly
        690                 695                 700 act ccc tgc tcc cca aac aaa aat gat gtt tgt att gac ggg gtt tgt        2160
Thr Pro Cys Ser Pro Asn Lys Asn Asp Val Cys Ile Asp Gly Val Cys
705                 710                 715                 720 gaa cta gtg gga tgt gat cat gaa cta ggc tct aaa gca gtt tca gat        2208
Glu Leu Val Gly Cys Asp His Glu Leu Gly Ser Lys Ala Val Ser Asp
                725                 730                 735 gct tgt ggc gtt tgc aaa ggt gat aat tca act tgc aag ttt tat aaa        2256
Ala Cys Gly Val Cys Lys Gly Asp Asn Ser Thr Cys Lys Phe Tyr Lys
                740                 745                 750 ggc ctg tac ctc aac cag cat aaa gca aat gaa tat tat ccg gtg gtc        2304
Gly Leu Tyr Leu Asn Gln His Lys Ala Asn Glu Tyr Tyr Pro Val Val
            755                 760                 765 atc att cca gct ggc gcc cga agc atc gaa atc cag gag ctg cag gtt        2352
Ile Ile Pro Ala Gly Ala Arg Ser Ile Glu Ile Gln Glu Leu Gln Val
        770                 775                 780
```

```
tcc tcc agt tac ctc gca gtt cga agc ctc agt caa aag tat tac ctc    2400
Ser Ser Ser Tyr Leu Ala Val Arg Ser Leu Ser Gln Lys Tyr Tyr Leu
785                 790                 795                 800 acc ggg ggc tgg agc atc gac tgg cct ggg gag ttc ccc ttc gct ggg    2448
Thr Gly Gly Trp Ser Ile Asp Trp Pro Gly Glu Phe Pro Phe Ala Gly
                805                 810                 815 acc acg ttt gaa tac cag cgc tct ttc aac cgc ccg gaa cgt ctg tac    2496
Thr Thr Phe Glu Tyr Gln Arg Ser Phe Asn Arg Pro Glu Arg Leu Tyr
        820                 825                 830 gcg cca ggg ccc aca aat gag acg ctg gtc ttt gaa att ctg atg caa    2544
Ala Pro Gly Pro Thr Asn Glu Thr Leu Val Phe Glu Ile Leu Met Gln
    835                 840                 845 ggc aaa aat cca ggg ata gct tgg aag tat gca ctt ccc aag gtc atg    2592
Gly Lys Asn Pro Gly Ile Ala Trp Lys Tyr Ala Leu Pro Lys Val Met
850                 855                 860 aat gga act cca cca gcc aca aaa aga cct gcc tat acc tgg agt atc    2640
Asn Gly Thr Pro Pro Ala Thr Lys Arg Pro Ala Tyr Thr Trp Ser Ile
865                 870                 875                 880 gtg cag tca gag tgc tcc gtc tcc tgt ggt gga ggt tac ata aat gta    2688
Val Gln Ser Glu Cys Ser Val Ser Cys Gly Gly Gly Tyr Ile Asn Val
                885                 890                 895 aag gcc att tgc ttg cga gat caa aat act caa gtc aat tcc tca ttc    2736
Lys Ala Ile Cys Leu Arg Asp Gln Asn Thr Gln Val Asn Ser Ser Phe
        900                 905                 910 tgc agt gca aaa acc aag cca gta act gag ccc aaa atc tgc aac gct    2784
Cys Ser Ala Lys Thr Lys Pro Val Thr Glu Pro Lys Ile Cys Asn Ala
    915                 920                 925 ttc tcc tgc ccg gct tac tgg atg cca ggt gaa tgg agt aca tgc agc    2832
Phe Ser Cys Pro Ala Tyr Trp Met Pro Gly Glu Trp Ser Thr Cys Ser
930                 935                 940 aag gcc tgt gct gga ggc cag cag agc cga aag atc cag tgt gtg caa    2880
Lys Ala Cys Ala Gly Gly Gln Gln Ser Arg Lys Ile Gln Cys Val Gln
945                 950                 955                 960 aag aag ccc ttc caa aag gag gaa gca gtg ttg cat tct ctc tgt cca    2928
Lys Lys Pro Phe Gln Lys Glu Glu Ala Val Leu His Ser Leu Cys Pro
                965                 970                 975 gtg agc aca ccc act cag gtc caa gcc tgc aac agc cat gcc tgc cct    2976
Val Ser Thr Pro Thr Gln Val Gln Ala Cys Asn Ser His Ala Cys Pro
        980                 985                 990 cca caa tgg agc ctt gga ccc tgg tct cag tgt tcc aag acc tgt gga    3024
Pro Gln Trp Ser Leu Gly Pro Trp Ser Gln Cys Ser Lys Thr Cys Gly
    995                 1000                1005 cga ggg gtg agg aag cgt gaa ctc ctc tgc aag ggc tct gcc gca gaa    3072
Arg Gly Val Arg Lys Arg Glu Leu Leu Cys Lys Gly Ser Ala Ala Glu
1010                1015                1020 acc ctc ccc gag agc cag tgt acc agt ctc ccc aga cct gag ctg cag    3120
Thr Leu Pro Glu Ser Gln Cys Thr Ser Leu Pro Arg Pro Glu Leu Gln
1025                1030                1035                1040 gag ggc tgt gtg ctt gga cga tgc ccc aag aac agc cgg cta cag tgg    3168
Glu Gly Cys Val Leu Gly Arg Cys Pro Lys Asn Ser Arg Leu Gln Trp
                1045                1050                1055 gtc gct tct tcg tgg agc gag tgt tct gca acc tgt ggt ttg ggt gtg    3216
Val Ala Ser Ser Trp Ser Glu Cys Ser Ala Thr Cys Gly Leu Gly Val
        1060                1065                1070 agg aag agg gag atg aag tgc agc gag aag ggc ttc cag gga aag ctg    3264
Arg Lys Arg Glu Met Lys Cys Ser Glu Lys Gly Phe Gln Gly Lys Leu
    1075                1080                1085 ata act ttc cca gag cga aga tgc cgt aat att aag aaa cca aat ctg    3312
Ile Thr Phe Pro Glu Arg Arg Cys Arg Asn Ile Lys Lys Pro Asn Leu
```

-continued

```
                1090                1095                1100
gac ttg gaa gag acc tgc aac cga cgg gct tgc cca gcc cat cca gtg    3360
Asp Leu Glu Glu Thr Cys Asn Arg Arg Ala Cys Pro Ala His Pro Val
   1105                1110                1115                1120 tac aac atg gta gct gga tgg tat tca ttg ccg tgg cag cag tgc aca    3408
Tyr Asn Met Val Ala Gly Trp Tyr Ser Leu Pro Trp Gln Gln Cys Thr
            1125                1130                1135 gtc acc tgt ggg gga ggg gtc cag acc cgg tca gtc cac tgt gtt cag    3456
Val Thr Cys Gly Gly Gly Val Gln Thr Arg Ser Val His Cys Val Gln
        1140                1145                1150 caa ggc cgg cct tcc tca agt tgt ctg ctc cat cag aaa cct ccg gtg    3504
Gln Gly Arg Pro Ser Ser Ser Cys Leu Leu His Gln Lys Pro Pro Val
    1155                1160                1165 cta cga gcc tgt aat aca aac ttc tgt cca gct cct gaa aag aga gag    3552
Leu Arg Ala Cys Asn Thr Asn Phe Cys Pro Ala Pro Glu Lys Arg Glu
   1170                1175                1180 gat cca tcc tgc gta gat ttc ttc aac tgg tgt cac cta gtt cct cag    3600
Asp Pro Ser Cys Val Asp Phe Phe Asn Trp Cys His Leu Val Pro Gln
1185                1190                1195                1200 cat ggt gtc tgc aac cac aag ttt tac gga aaa caa tgc tgc aag tca    3648
His Gly Val Cys Asn His Lys Phe Tyr Gly Lys Gln Cys Cys Lys Ser
            1205                1210                1215 tgc aca agg aag atc tga                                             3666
Cys Thr Arg Lys Ile
        1220

<210> SEQ ID NO 2
<211> LENGTH: 1221
<212> TYPE: PRT
<213> ORGANISM: Homo sapiens

<400> SEQUENCE: 2

Met Glu Cys Ala Leu Leu Leu Ala Cys Ala Phe Pro Ala Ala Gly Ser
 1               5                  10                  15

Gly Pro Pro Arg Gly Leu Ala Gly Leu Gly Arg Val Ala Lys Ala Leu
            20                  25                  30

Gln Leu Cys Cys Leu Cys Cys Ala Ser Val Ala Ala Ala Leu Ala Ser
        35                  40                  45

Asp Ser Ser Ser Gly Ala Ser Gly Leu Asn Asp Asp Tyr Val Phe Val
    50                  55                  60

Thr Pro Val Glu Val Asp Ser Ala Gly Ser Tyr Ile Ser His Asp Ile
65                  70                  75                  80

Leu His Asn Gly Arg Lys Lys Arg Ser Ala Gln Asn Ala Arg Ser Ser
                85                  90                  95

Leu His Tyr Arg Phe Ser Ala Phe Gly Gln Glu Leu His Leu Glu Leu
            100                 105                 110

Lys Pro Ser Ala Ile Leu Ser Ser His Phe Ile Val Gln Val Leu Gly
        115                 120                 125

Lys Asp Gly Ala Ser Glu Thr Gln Lys Pro Glu Val Gln Gln Cys Phe
    130                 135                 140

Tyr Gln Gly Phe Ile Arg Asn Asp Ser Ser Ser Val Ala Val Ser
145                 150                 155                 160

Thr Cys Ala Gly Leu Ser Gly Leu Ile Arg Thr Arg Lys Asn Glu Phe
                165                 170                 175

Leu Ile Ser Pro Leu Pro Gln Leu Leu Ala Gln Glu His Asn Tyr Ser
            180                 185                 190

Ser Pro Ala Gly His His Pro His Val Leu Tyr Lys Arg Thr Ala Glu
```

-continued

```
                195                 200                 205
Glu Lys Ile Gln Arg Tyr Arg Gly Tyr Pro Gly Ser Gly Arg Asn Tyr
    210                 215                 220

Pro Gly Tyr Ser Pro Ser His Ile Pro His Ala Ser Gln Ser Arg Glu
225                 230                 235                 240

Thr Glu Tyr His His Arg Arg Leu Gln Lys Gln His Phe Cys Gly Arg
                245                 250                 255

Arg Lys Lys Tyr Ala Pro Lys Pro Pro Thr Glu Asp Thr Tyr Leu Arg
                260                 265                 270

Phe Asp Glu Tyr Gly Ser Ser Gly Arg Pro Arg Arg Ser Ala Gly Lys
            275                 280                 285

Ser Gln Lys Gly Leu Asn Val Glu Thr Leu Val Val Ala Asp Lys Lys
        290                 295                 300

Met Val Glu Lys His Gly Lys Gly Asn Val Thr Thr Tyr Ile Leu Thr
305                 310                 315                 320

Val Met Asn Met Val Ser Gly Leu Phe Lys Asp Gly Thr Ile Gly Ser
                325                 330                 335

Asp Ile Asn Val Val Val Ser Leu Ile Leu Leu Glu Gln Glu Pro
                340                 345                 350

Gly Gly Leu Leu Ile Asn His His Ala Asp Gln Ser Leu Asn Ser Phe
            355                 360                 365

Cys Gln Trp Gln Ser Ala Leu Ile Gly Lys Asn Gly Lys Arg His Asp
    370                 375                 380

His Ala Ile Leu Leu Thr Gly Phe Asp Ile Cys Ser Trp Lys Asn Glu
385                 390                 395                 400

Pro Cys Asp Thr Leu Gly Phe Ala Pro Ile Ser Gly Met Cys Ser Lys
                405                 410                 415

Tyr Arg Ser Cys Thr Ile Asn Glu Asp Thr Gly Leu Gly Leu Ala Phe
            420                 425                 430

Thr Ile Ala His Glu Ser Gly His Asn Phe Gly Met Ile His Asp Gly
        435                 440                 445

Glu Gly Asn Pro Cys Arg Lys Ala Glu Gly Asn Ile Met Ser Pro Thr
    450                 455                 460

Leu Thr Gly Asn Asn Gly Val Phe Ser Trp Ser Ser Cys Ser Arg Gln
465                 470                 475                 480

Tyr Leu Lys Lys Phe Leu Ser Thr Pro Gln Ala Gly Cys Leu Val Asp
                485                 490                 495

Glu Pro Lys Gln Ala Gly Gln Tyr Lys Tyr Pro Asp Lys Leu Pro Gly
            500                 505                 510

Gln Ile Tyr Asp Ala Asp Thr Gln Cys Lys Trp Gln Phe Gly Ala Lys
        515                 520                 525

Ala Lys Leu Cys Ser Leu Gly Phe Val Lys Asp Ile Cys Lys Ser Leu
    530                 535                 540

Trp Cys His Arg Val Gly His Arg Cys Glu Thr Lys Phe Met Pro Ala
545                 550                 555                 560

Ala Glu Gly Thr Val Cys Gly Leu Ser Met Trp Cys Arg Gln Gly Gln
                565                 570                 575

Cys Val Lys Phe Gly Glu Leu Gly Pro Arg Pro Ile His Gly Gln Trp
            580                 585                 590

Ser Ala Trp Ser Lys Trp Ser Glu Cys Ser Arg Thr Cys Gly Gly Gly
        595                 600                 605

Val Lys Phe Gln Glu Arg His Cys Asn Asn Pro Lys Pro Gln Tyr Gly
    610                 615                 620
```

-continued

```
Gly Leu Phe Cys Pro Gly Ser Ser Arg Ile Tyr Gln Leu Cys Asn Ile
625                 630                 635                 640

Asn Pro Cys Asn Glu Asn Ser Leu Asp Phe Arg Ala Gln Gln Cys Ala
                645                 650                 655

Glu Tyr Asn Ser Lys Pro Phe Arg Gly Trp Phe Tyr Gln Trp Lys Pro
                660                 665                 670

Tyr Thr Lys Val Glu Glu Asp Arg Cys Lys Leu Tyr Cys Lys Ala
                675                 680                 685

Glu Asn Phe Glu Phe Phe Ala Met Ser Gly Lys Val Lys Asp Gly
690                 695                 700

Thr Pro Cys Ser Pro Asn Lys Asn Asp Val Cys Ile Asp Gly Val Cys
705                 710                 715                 720

Glu Leu Val Gly Cys Asp His Glu Leu Gly Ser Lys Ala Val Ser Asp
                725                 730                 735

Ala Cys Gly Val Cys Lys Gly Asp Asn Ser Thr Cys Lys Phe Tyr Lys
                740                 745                 750

Gly Leu Tyr Leu Asn Gln His Lys Ala Asn Glu Tyr Tyr Pro Val Val
                755                 760                 765

Ile Ile Pro Ala Gly Ala Arg Ser Ile Glu Ile Gln Glu Leu Gln Val
770                 775                 780

Ser Ser Ser Tyr Leu Ala Val Arg Ser Leu Ser Gln Lys Tyr Tyr Leu
785                 790                 795                 800

Thr Gly Gly Trp Ser Ile Asp Trp Pro Gly Glu Phe Pro Phe Ala Gly
                805                 810                 815

Thr Thr Phe Glu Tyr Gln Arg Ser Phe Asn Arg Pro Glu Arg Leu Tyr
                820                 825                 830

Ala Pro Gly Pro Thr Asn Glu Thr Leu Val Phe Glu Ile Leu Met Gln
                835                 840                 845

Gly Lys Asn Pro Gly Ile Ala Trp Lys Tyr Ala Leu Pro Lys Val Met
850                 855                 860

Asn Gly Thr Pro Pro Ala Thr Lys Arg Pro Ala Tyr Thr Trp Ser Ile
865                 870                 875                 880

Val Gln Ser Glu Cys Ser Val Ser Cys Gly Gly Gly Tyr Ile Asn Val
                885                 890                 895

Lys Ala Ile Cys Leu Arg Asp Gln Asn Thr Gln Val Asn Ser Ser Phe
                900                 905                 910

Cys Ser Ala Lys Thr Lys Pro Val Thr Glu Pro Lys Ile Cys Asn Ala
                915                 920                 925

Phe Ser Cys Pro Ala Tyr Trp Met Pro Gly Glu Trp Ser Thr Cys Ser
930                 935                 940

Lys Ala Cys Ala Gly Gly Gln Gln Ser Arg Lys Ile Gln Cys Val Gln
945                 950                 955                 960

Lys Lys Pro Phe Gln Lys Glu Glu Ala Val Leu His Ser Leu Cys Pro
                965                 970                 975

Val Ser Thr Pro Thr Gln Val Gln Ala Cys Asn Ser His Ala Cys Pro
                980                 985                 990

Pro Gln Trp Ser Leu Gly Pro Trp Ser Gln Cys Ser Lys Thr Cys Gly
                995                 1000                1005

Arg Gly Val Arg Lys Arg Glu Leu Leu Cys Lys Gly Ser Ala Ala Glu
    1010                1015                1020

Thr Leu Pro Glu Ser Gln Cys Thr Ser Leu Pro Arg Pro Glu Leu Gln
1025                1030                1035                1040
```

```
Glu Gly Cys Val Leu Gly Arg Cys Pro Lys Asn Ser Arg Leu Gln Trp
            1045                1050                1055

Val Ala Ser Ser Trp Ser Glu Cys Ser Ala Thr Cys Gly Leu Gly Val
        1060                1065                1070

Arg Lys Arg Glu Met Lys Cys Ser Glu Lys Gly Phe Gln Gly Lys Leu
    1075                1080                1085

Ile Thr Phe Pro Glu Arg Arg Cys Arg Asn Ile Lys Lys Pro Asn Leu
        1090                1095                1100

Asp Leu Glu Glu Thr Cys Asn Arg Arg Ala Cys Pro Ala His Pro Val
1105                1110                1115                1120

Tyr Asn Met Val Ala Gly Trp Tyr Ser Leu Pro Trp Gln Gln Cys Thr
            1125                1130                1135

Val Thr Cys Gly Gly Gly Val Gln Thr Arg Ser Val His Cys Val Gln
        1140                1145                1150

Gln Gly Arg Pro Ser Ser Ser Cys Leu Leu His Gln Lys Pro Pro Val
    1155                1160                1165

Leu Arg Ala Cys Asn Thr Asn Phe Cys Pro Ala Pro Glu Lys Arg Glu
    1170                1175                1180

Asp Pro Ser Cys Val Asp Phe Phe Asn Trp Cys His Leu Val Pro Gln
1185                1190                1195                1200

His Gly Val Cys Asn His Lys Phe Tyr Gly Lys Gln Cys Cys Lys Ser
            1205                1210                1215

Cys Thr Arg Lys Ile
            1220

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 3
gctctagacc atggagtgcg ccctcctgct cgcgtgtgcc                          40

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 4
agagcggccg cgcctttata aaacttgcaa gttgaattat c                        41

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 5
acggggtttg tgaactagtg ggatgtga                                       28

<210> SEQ ID NO 6
<211> LENGTH: 41
<212> TYPE: DNA
```

```
<213> ORGANISM: Artificial Sequence
<220> FEATURE:
<223> OTHER INFORMATION: Description of Artificial Sequence: an
      artificially synthesized primer sequence

<400> SEQUENCE: 6
agagcggccg cgatcttcct tgtgcatgac ttgcagcatt g                          41

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: an
      artificially synthesized linker sequence

<400> SEQUENCE: 7
ctagcgcggc cgcaggatcc gactacaagg acgacgatga caaatgataa                 50

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: an
      artificially synthesized linker sequence

<400> SEQUENCE: 8
gatcttatca tttgtcatcg tcgtccttgt agtcggatcc tgcggccgcg                 50

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 9
ggactagtct agaagctggg taccagctgc tagc                                  34

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 10
ggactagtgt cgaccggtca tggctgcgc                                        29

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 11
taggatcctt gtagaaactt cagaccatga caactcg                               37

<210> SEQ ID NO 12
<211> LENGTH: 59
<212> TYPE: DNA
<213> ORGANISM: Artificial Sequence
```

-continued

```
<220> FEATURE:
<223> OTHER INFORMATION: Description of Artificial Sequence: an
      artificially synthesized primer sequence

<400> SEQUENCE: 12
atggatcctc aatggtgatg gtgatgatga ccgaagcaga aggcatggtg ccgggacag      59

<210> SEQ ID NO 13
<211> LENGTH: 97
<212> TYPE: DNA
<213> ORGANISM: Artificial Sequence
<220> FEATURE:
<223> OTHER INFORMATION: Description of Artificial Sequence: an
      artificially synthesized linker sequence

<400> SEQUENCE: 13
agcttgccac catgaagacg atcatcgccc tgagctacat cttctgcctg gtattcgccg      60
actacaagga cgatgatgac aagggatcc actagtc                               97

<210> SEQ ID NO 14
<211> LENGTH: 97
<212> TYPE: DNA
<213> ORGANISM: Artificial Sequence
<220> FEATURE:
<223> OTHER INFORMATION: Description of Artificial Sequence: an
      artificially synthesized linker sequence

<400> SEQUENCE: 14
tcgagactag tggatccct tgtcatcatc gtccttgtag tcggcgaata ccaggcagaa      60
gatgtagctc agggcgatga tcgtcttcat ggtggca                              97

<210> SEQ ID NO 15
<211> LENGTH: 20
<212> TYPE: DNA
<213> ORGANISM: Homo sapiens

<400> SEQUENCE: 15
tttcccaggt caagatggtc                                                 20

<210> SEQ ID NO 16
<211> LENGTH: 20
<212> TYPE: DNA
<213> ORGANISM: Homo sapiens

<400> SEQUENCE: 16
cttcagcacc tgtctcacca                                                 20

<210> SEQ ID NO 17
<211> LENGTH: 20
<212> TYPE: DNA
<213> ORGANISM: Homo sapiens

<400> SEQUENCE: 17
gtgttgctgg tgaaaagggt                                                 20

<210> SEQ ID NO 18
<211> LENGTH: 20
<212> TYPE: DNA
<213> ORGANISM: Homo sapiens

<400> SEQUENCE: 18
gggatcccac tggtcctaat                                                 20
```

```
<210> SEQ ID NO 19
<211> LENGTH: 30
<212> TYPE: DNA
<213> ORGANISM: Homo sapiens

<400> SEQUENCE: 19
cagtggaatg tgctctaagt accgaagttg                                      30

<210> SEQ ID NO 20
<211> LENGTH: 30
<212> TYPE: DNA
<213> ORGANISM: Homo sapiens

<400> SEQUENCE: 20
acactgtgtg tcagcatcat aaatctgtcc                                      30

<210> SEQ ID NO 21
<211> LENGTH: 22
<212> TYPE: DNA
<213> ORGANISM: Homo sapiens

<400> SEQUENCE: 21
caacgaattt ggctacagca ac                                              22

<210> SEQ ID NO 22
<211> LENGTH: 22
<212> TYPE: DNA
<213> ORGANISM: Homo sapiens

<400> SEQUENCE: 22
ctacatggca actgtgagga gg                                              22

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: an
      artificially synthesized sequence containing a restriction
      enzyme NotI recognition sequence and
      a FLAG tag sequence

<400> SEQUENCE: 23

Ala Ala Ala Asp Tyr Lys Asp Asp Asp Asp Lys
 1               5                  10

<210> SEQ ID NO 24
<211> LENGTH: 5
<212> TYPE: PRT
<213> ORGANISM: Homo sapiens
<220> FEATURE:
<221> NAME/KEY: misc_feature
<222> LOCATION: (3)..(4)
<223> OTHER INFORMATION: Xaa is any amino acid

<400> SEQUENCE: 24

His Glu Xaa Xaa His
 1               5

<210> SEQ ID NO 25
<211> LENGTH: 5
<212> TYPE: PRT
<213> ORGANISM: Homo sapiens
```

```
-continued

<400> SEQUENCE: 25

Asn Ile Thr Gly Glu
  1               5

<210> SEQ ID NO 26
<211> LENGTH: 5
<212> TYPE: PRT
<213> ORGANISM: Homo sapiens

<400> SEQUENCE: 26

Ala Arg Gly Ser Val
  1               5
```